US012521048B2

(12) United States Patent
Takenaka et al.

(10) Patent No.: US 12,521,048 B2
(45) Date of Patent: Jan. 13, 2026

(54) BLOOD COLLECTION APPARATUS

(71) Applicant: Hitachi High-Tech Corporation, Tokyo (JP)

(72) Inventors: Kei Takenaka, Tokyo (JP); Shigenori Togashi, Tokyo (JP); Seiichi Boku, Tokyo (JP); Takashi Irie, Tokyo (JP); Taku Sakazume, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 805 days.

(21) Appl. No.: 17/622,911

(22) PCT Filed: Jun. 2, 2020

(86) PCT No.: PCT/JP2020/021793
§ 371 (c)(1),
(2) Date: Dec. 27, 2021

(87) PCT Pub. No.: WO2021/014771
PCT Pub. Date: Jan. 28, 2021

(65) Prior Publication Data

US 2022/0257157 A1 Aug. 18, 2022

(30) Foreign Application Priority Data

Jul. 19, 2019 (JP) ................................ 2019-133951

(51) Int. Cl.
*A61B 5/15* (2006.01)
*A61B 5/151* (2006.01)

(52) U.S. Cl.
CPC .. *A61B 5/150068* (2013.01); *A61B 5/150022* (2013.01); *A61B 5/150198* (2013.01);
(Continued)

(58) Field of Classification Search
CPC ........ A61B 5/150022; A61B 5/150198; A61B 5/150374; A61B 5/150412; A61B 5/15107
See application file for complete search history.

(56) References Cited

U.S. PATENT DOCUMENTS

2018/0220944 A1 8/2018 Otsubo et al.

FOREIGN PATENT DOCUMENTS

JP 2003-325485 A 11/2003
JP 2017-225519 A 12/2017
(Continued)

OTHER PUBLICATIONS

International Search Report of PCT/JP2020/021793 dated Aug. 25, 2020.

*Primary Examiner* — Jennifer Robertson
*Assistant Examiner* — Om Patel
(74) *Attorney, Agent, or Firm* — MATTINGLY & MALUR, PC

(57) ABSTRACT

Provided is a blood collection apparatus with which blood can be stably collected from a finger tip of any subject while ensuring safety and ease. This blood collection apparatus is provided with: a puncture site holding mechanism for holding a puncture site; a compression mechanism for performing an operation of compressing and releasing the puncture site when blood is collected from the puncture site; a container holding mechanism for holding a container for collecting blood flowing from a puncture wound at the puncture site; and a driving mechanism for varying the relative distance between the puncture site and the container by vertically moving the puncture site holding mechanism, the container holding mechanism, or the container held by the container holding mechanism when blood flowing from the puncture wound is collected.

17 Claims, 19 Drawing Sheets

(52) U.S. Cl.
CPC .. *A61B 5/150374* (2013.01); *A61B 5/150412* (2013.01); *A61B 5/15107* (2013.01)

(56) References Cited

FOREIGN PATENT DOCUMENTS

| | | | |
|---|---|---|---|
| JP | 2019-047893 | A | 3/2019 |
| WO | 2016/203853 | A1 | 12/2016 |
| WO | 2017/221698 | A1 | 12/2017 |
| WO | 2019/093124 | A1 | 5/2019 |

BLOOD COLLECTION APPARATUS

TECHNICAL FIELD

The present invention relates to a blood collection apparatus which collects blood from a finger of a subject (blood collection subject).

BACKGROUND ART

It is important to have regular medical checkups in order to live a healthy life. One of tests commonly and frequently performed in medical checkups is a blood test for diagnosing states of tissues and organs of the whole body by collecting blood from a subject and analyzing components of the blood. A general blood test is often performed in a medical institution, but is often performed at home as a self-test with a limited measurement item such as a blood glucose level.

A blood collection method that is often performed as blood collection for a self-test, such as blood glucose level measurement, is capillary blood collection. The capillary blood collection is a method of pressing a dedicated skin puncture tool against a finger of a subject to puncture a capillary of the finger and collecting blood that flows out. The capillary blood collection is a simpler blood collection method than venous blood collection. However, the amount of blood that can be secured is small, and thus, complicated work such as compressing and squeezing the finger during blood collection is required to secure the blood collection amount.

PTL 1 discloses a blood collection apparatus that automates blood collection from a finger. The blood collection apparatus includes: a cartridge that holds a puncture tool, a blood collection tube, and an adhesive bandage; a driving mechanism for changing a position of the cartridge and performing an operation of pressing the puncture tool, a container, and a seal against a finger tip; a fixing mechanism for fixing a part of the finger tip; and a compression mechanism for compressing a root of the finger, and pierces the finger tip of a subject with the puncture tool after compressing the root of the finger, collects blood from a puncture wound into the blood collection tube, and the compression is released, and then staunches bleeding from the puncture wound with the adhesive bandage.

CITATION LIST

Patent Literature

PTL 1: JP 2017-225519 A

SUMMARY OF INVENTION

Technical Problem

The blood collection apparatus described in PTL 1 is advantageous in that the blood collection subject can perform blood collection from the finger tip without complicated work. However, there is an individual difference in the diathesis of the blood collection subject according to studies of the present inventors, and there is a possibility that it is difficult to perform stable blood collection and a sufficient blood collection amount is hardly secured even in the blood collection apparatus described in PTL 1.

An object of the present invention is to provide a blood collection apparatus with which blood can be stably collected from a finger tip of any subject while ensuring safety and ease.

Solution to Problem

In order to achieve the above object, a blood collection apparatus of the present invention has a configuration described in the claims. For example, the blood collection apparatus is provided with: a puncture site holding mechanism for holding a puncture site of a subject; a compression mechanism for performing an operation of compressing and releasing the puncture site when blood is collected from the puncture site; a container holding mechanism for holding a container for collecting blood flowing from a puncture wound at the puncture site; and a driving mechanism for varying the relative distance between the puncture site and the container by vertically moving the puncture site holding mechanism, the container holding mechanism, or the container held by the container holding mechanism when blood flowing from the puncture wound is collected.

Advantageous Effects of Invention

According to the blood collection apparatus of the present invention, it is possible to stably collect the blood from the finger tip of any subject while ensuring the safety and ease.

Other objects, configurations, and effects which have not been described above become apparent from embodiments to be described hereinafter.

DESCRIPTION OF EMBODIMENTS

Hereinafter, an embodiment of the present invention will be described with reference to the drawings. Note that embodiments to be described later are merely examples, and it goes without saying that other modes obtained by combination of the respective embodiments and combination or replacement with a known or well-known technique are also possible.

In addition, the description of the claims is given with a single claim in order to simplify the citation relationship, but the present invention also includes a case where a multi-claim is used and a case where a multi-multi claim is used.

First, circumstances leading to the present invention will be described.

Since blood collection from a subject is essential to perform a blood test, it is preferable that anyone can easily and safely collect blood. Therefore, the present inventors have studied various automatic blood collection methods and systems, and have proposed a blood collection apparatus described in PTL 1. With the blood collection apparatus described in PTL 1, anyone can easily and safely collect blood. According to the studies of the present inventors, however, it has been found that blood is coagulated in a puncture wound and it becomes difficult to perform stable blood collection, for example, when the amount of blood flowing out from the puncture wound is small and a state in which the blood remains on a finger tip is prolonged even if compression and release are repeated depending on the diathesis of a subject or the like. Therefore, a blood collection apparatus having a function of actively promoting bleeding from a finger tip is required in order to constantly realize stable blood collection for any subject. As a result of various studies, the present inventors have found that the blood remaining on the finger tip when the blood collection tube is separated from the finger tip is separated from the finger tip to promote movement of the blood toward the blood collection tube by repeatedly changing a relative distance between the blood collection tube and the finger tip in addition to compression and release of a finger so that the blood coagulation at the puncture wound is suppressed. Since the blood coagulation at the puncture wound is suppressed, the stable blood collection can be realized by repeating the compression and release of the finger.

Next, a basic configuration of a blood collection apparatus 1 according to the embodiment of the present invention will be described with reference to FIGS. 1 and 2.

Figure 1:
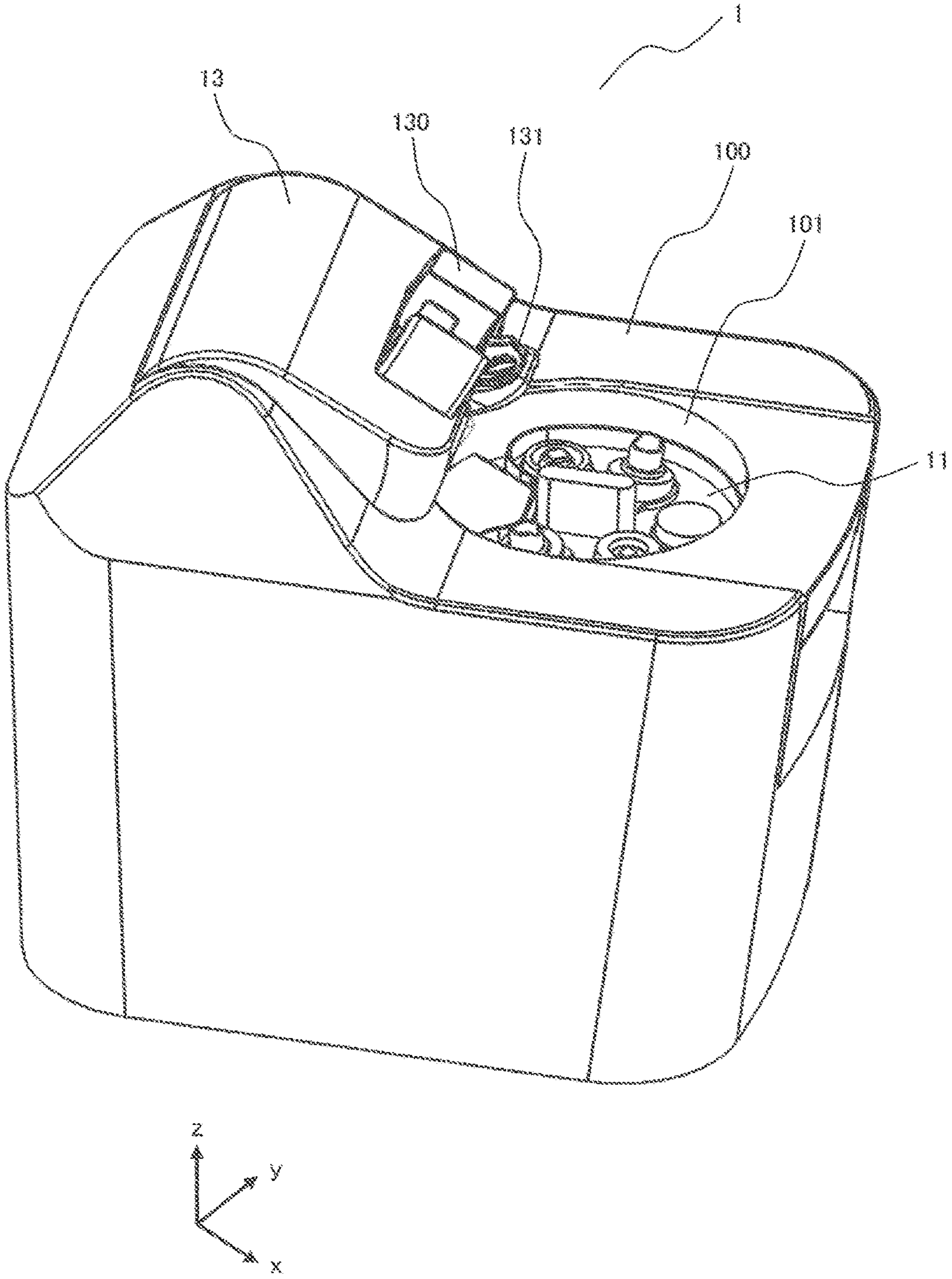
FIG. 1 is a view illustrating an appearance of a blood collection apparatus according to an embodiment of the present invention.
Figure 2:
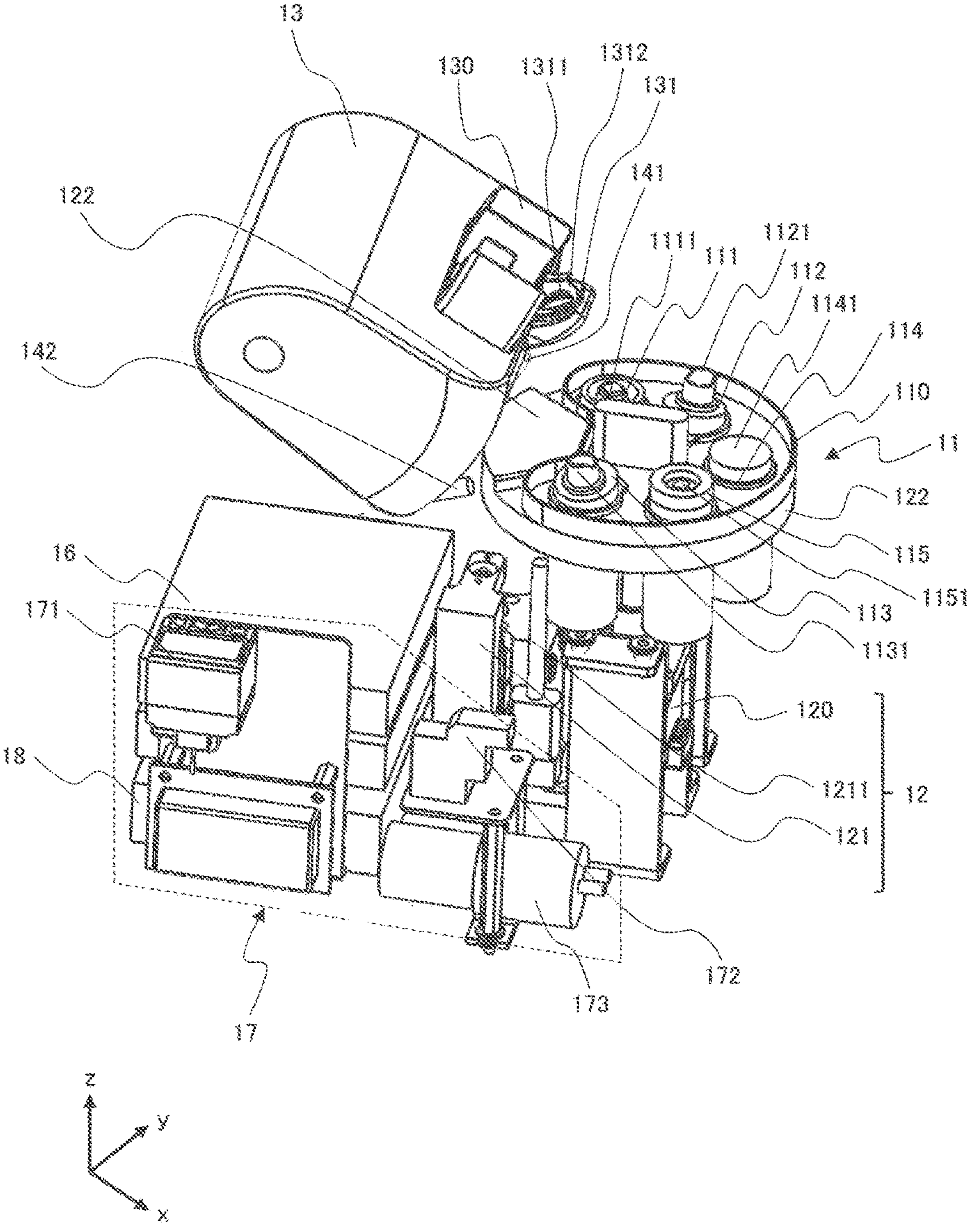
FIG. 2 is an internal configuration diagram of the blood collection apparatus according to the embodiment of the present invention.

FIG. 1 is a basic configuration diagram of the blood collection apparatus 1, and FIG. 2 is an internal configuration diagram of the blood collection apparatus 1 from which a case 100 is removed. The blood collection apparatus 1 includes: a cartridge 11 including a puncture tool 1111, a blood-count blood collection tube 1121, a biochemical and immunological blood collection tube 1131, a gauze 1141, and an adhesive bandage 1151; a driving mechanism for controlling movement of the cartridge 11; a cuff mechanism finger fixing unit 13 including a cuff mechanism 130 for tightening a periphery of a finger (puncture site; not illustrated in FIGS. 1 and 2) of a subject; a pressure adjustment mechanism 17 for adjusting the pressure of the cuff mechanism 130; a control mechanism 16 for controlling operations of the driving mechanism 12 and the pressure adjustment mechanism 17; cameras 141 and 142 configured for image measurement of a finger tip position and the amount of collected blood; and an input/output device (not illustrated) configured to take images of the cameras, input an instruction content to the control mechanism 16, and display an output result from the control mechanism 16. As the input/output device, a personal computer or a tablet PC connected to the blood collection apparatus 1 can be used.

The driving mechanism 12 includes a rotational-direction driving mechanism 120 and a vertical-direction driving mechanism 121. The rotational-direction driving mechanism 120 rotates the cartridge 11 in a cartridge container 101 (with a z-axis as a rotation axis) through a cartridge holder 122 in which the cartridge 11 is set, and rotationally moves the cartridge 11 such that the puncture tool 1111, the blood-count blood collection tube 1121, the biochemical and immunological blood collection tube 1131, the gauze 1141, or the adhesive bandage (seal) 1151 is arranged immediately below a blood collection window 1311 of a finger placement portion 131 on which a finger to be subjected to blood collection is placed. The rotational-direction driving mechanism 120 also serves as a horizontal-direction driving mechanism for changing a relative position between the blood collection window 1311 of the finger placement portion 131, and the puncture tool, the blood collection tube, the gauze, or the adhesive bandage on a horizontal plane. The vertical-direction driving mechanism 121 includes a push rod 1211, and moves the puncture tool 1111, the blood-count blood collection tube 1121, the biochemical and immunological blood collection tube 1131, the gauze 1141, or the adhesive bandage 1151 arranged immediately below the blood collection window 1311 in the vertical direction (z direction) through the push rod 1211 to be brought close to or be pressed against a finger. The puncture tool 1111 is pressed against a finger to puncture a finger 153, the blood-count blood collection tube 1121 or the biochemical and immunological blood collection tube 1131 is brought close to the finger to collect blood from a puncture point without scattering the blood to the surroundings, the gauze 1141 is pressed against the finger to wipe off excess blood, and the adhesive bandage 1151 is pressed against the finger so that bleeding from the puncture point can be staunched. As a power source of the driving mechanism 12, a mechanical power source, such as a spring, may be used in addition to electrical energy such as an external power source and a built-in battery. When the spring is used as the power source, the use in an area where supply of electricity is difficult becomes possible.

The cuff mechanism finger fixing unit 13 includes the cuff mechanism 130 provided with a cuff configured to tighten a blood collection target finger and the finger placement portion 131 configured to place a blood collection target finger tip. The finger placement portion 131 further includes a disposable finger placement plate component 1312 at a point to be in contact with the finger. The finger placement plate component includes the blood collection window 1311 which is a void for blood collection.

The pressure adjustment mechanism 17 includes a cuff internal pressure sensor 171 configured to measure the internal pressure of the cuff of the cuff mechanism 130, and a cuff valve 172 and a cuff pump 173 configured to control the internal pressure of the cuff, and can adjust the tightening pressure of the blood collection target finger by controlling the internal pressure of the cuff.

Note that the cuff mechanism finger fixing unit 13 is a configuration example of a puncture site holding mechanism. The cuff mechanism 130 and the pressure adjustment mechanism 17 are configuration examples of a compression mechanism for performing an operation of compressing and releasing a puncture site at the time of collecting blood from the puncture site. The cartridge 11 is a configuration example of a container holding mechanism for holding a container for collecting blood flowing from a puncture wound of the puncture site. The driving mechanism 12 is a configuration example of a driving mechanism for varying the relative distance between the puncture site and the container by vertically moving the puncture site holding mechanism, the container holding mechanism, or the container held by the container holding mechanism when blood flowing from the puncture wound is collected.

Figure 3:
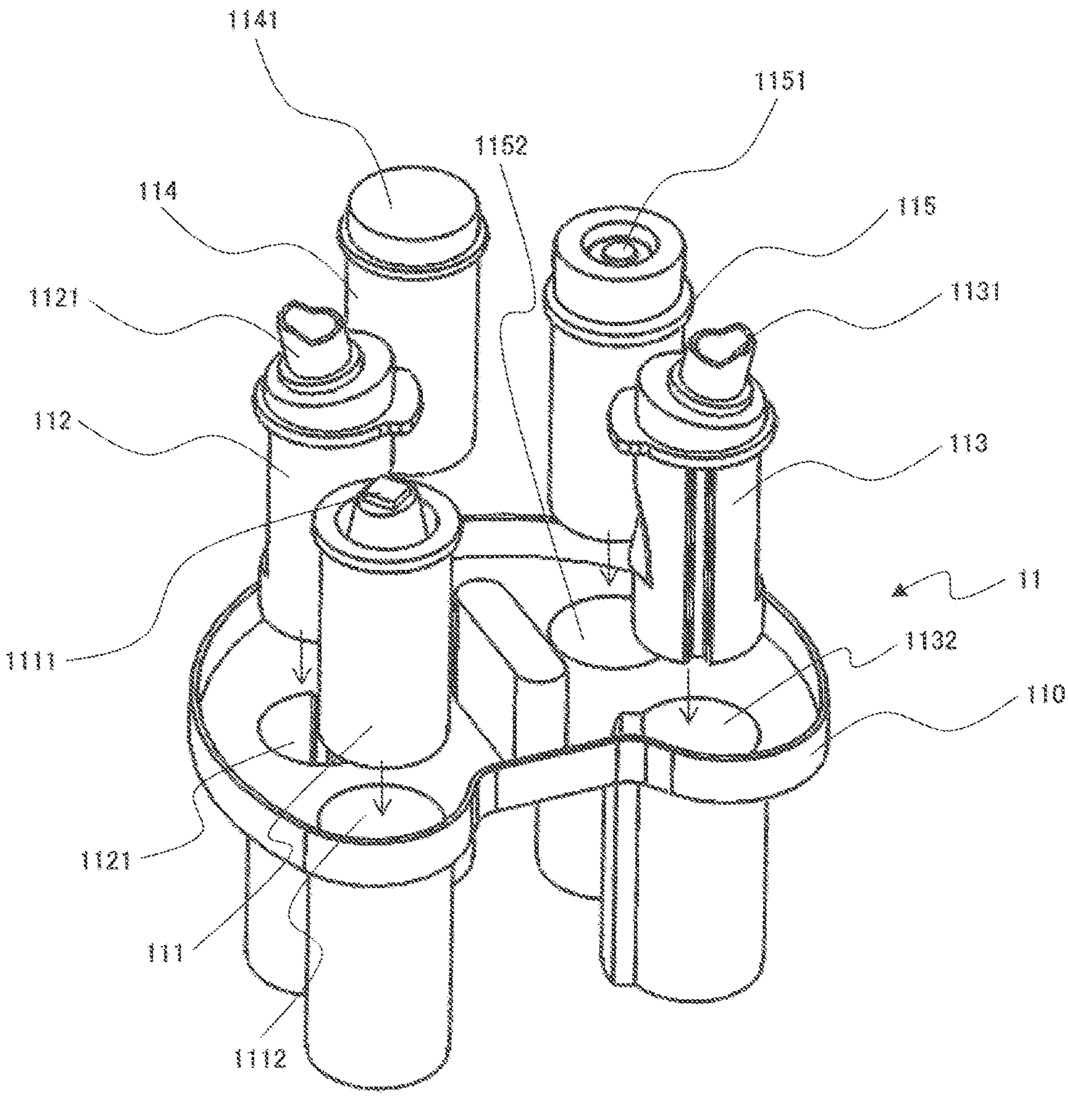
FIG. 3 is a view illustrating a configuration of a cartridge in the blood collection apparatus according to the embodiment of the present invention.
Figure 4:
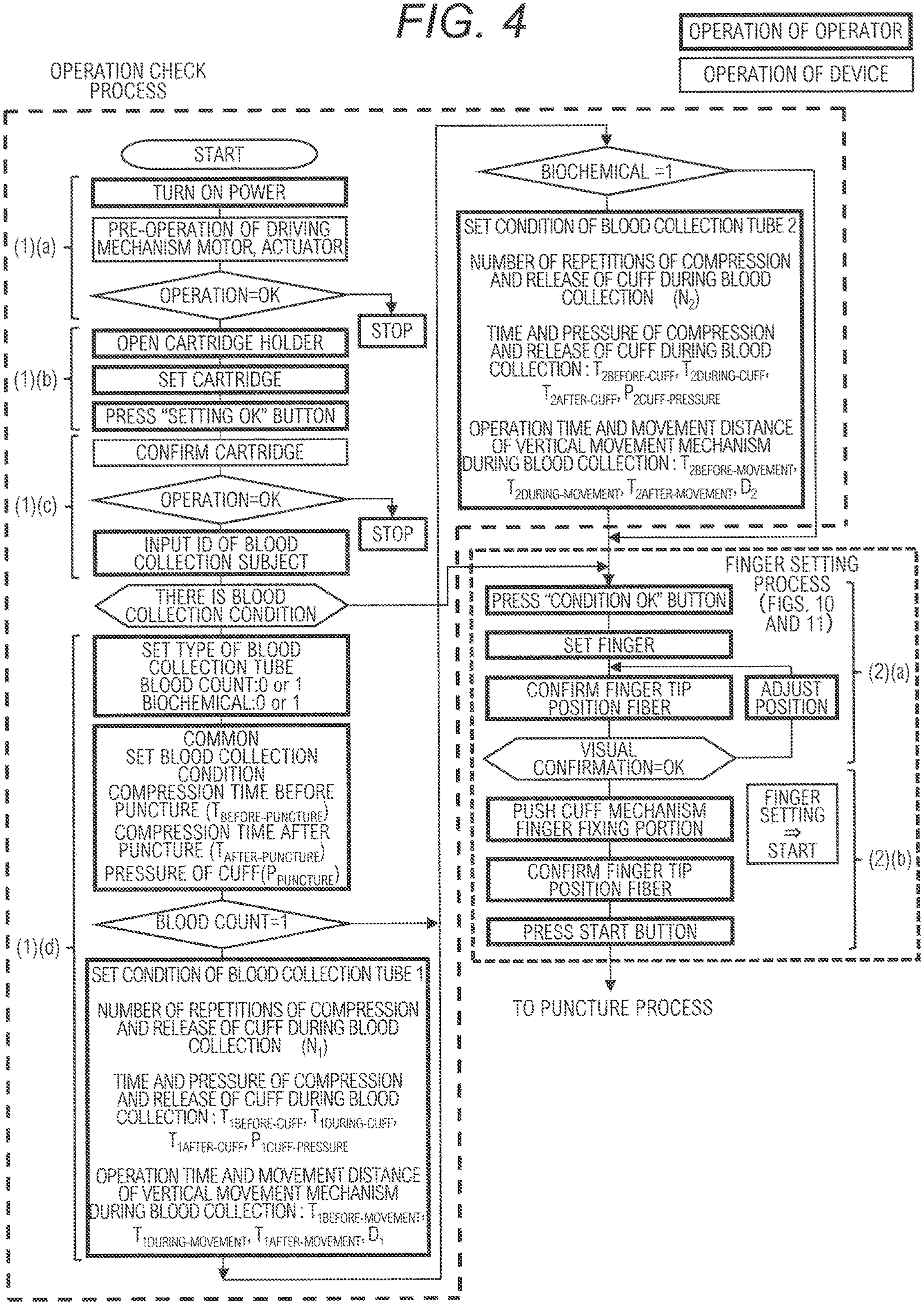
FIG. 4 is a flowchart of an operation check process and a finger setting process of blood collection by the blood collection apparatus according to the embodiment of the present invention.
Figure 5:
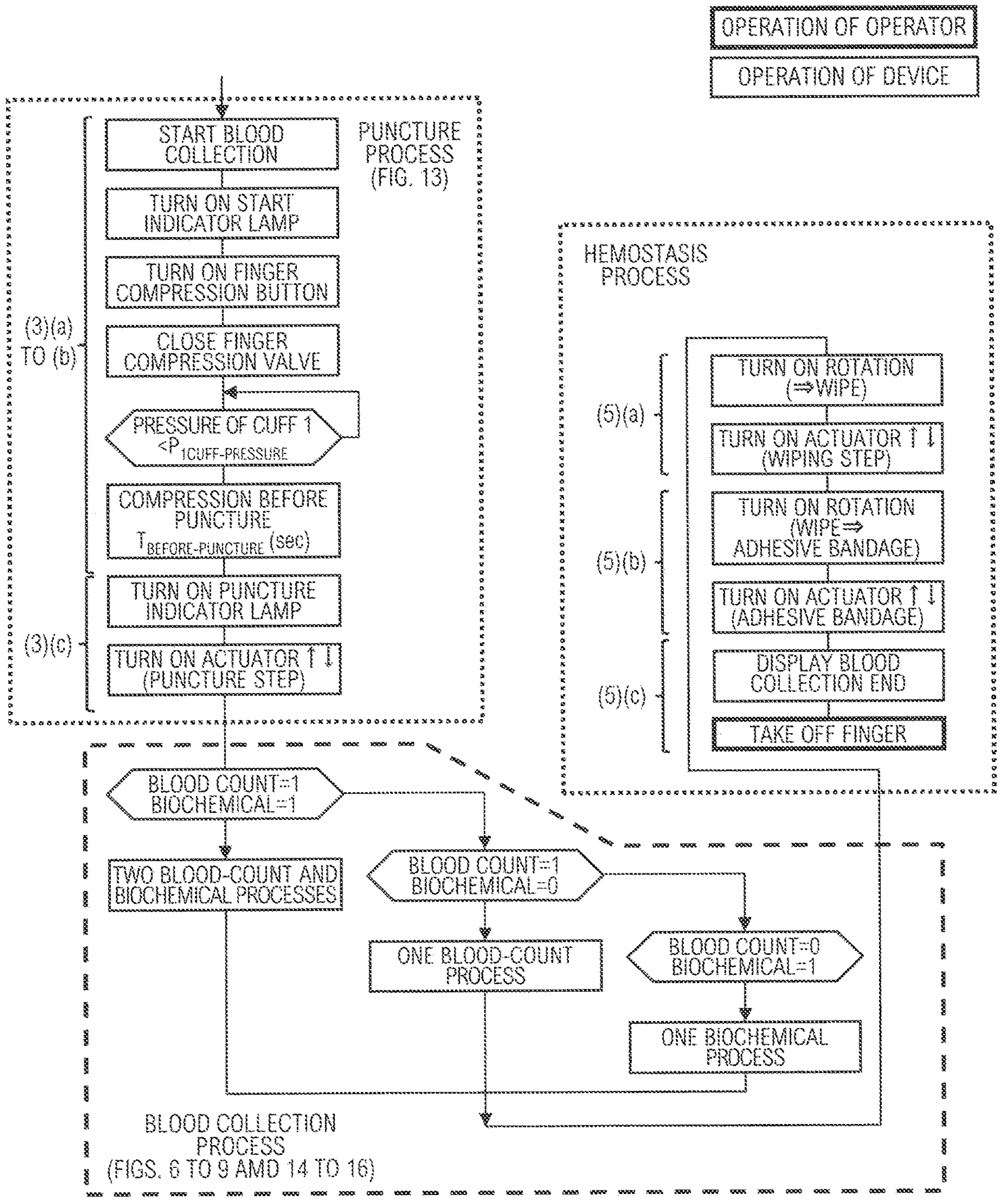
FIG. 5 is a flowchart of blood collection including a puncture process, a blood collection process, and a hemostasis process by the blood collection apparatus according to the embodiment of the present invention.
Figure 6:
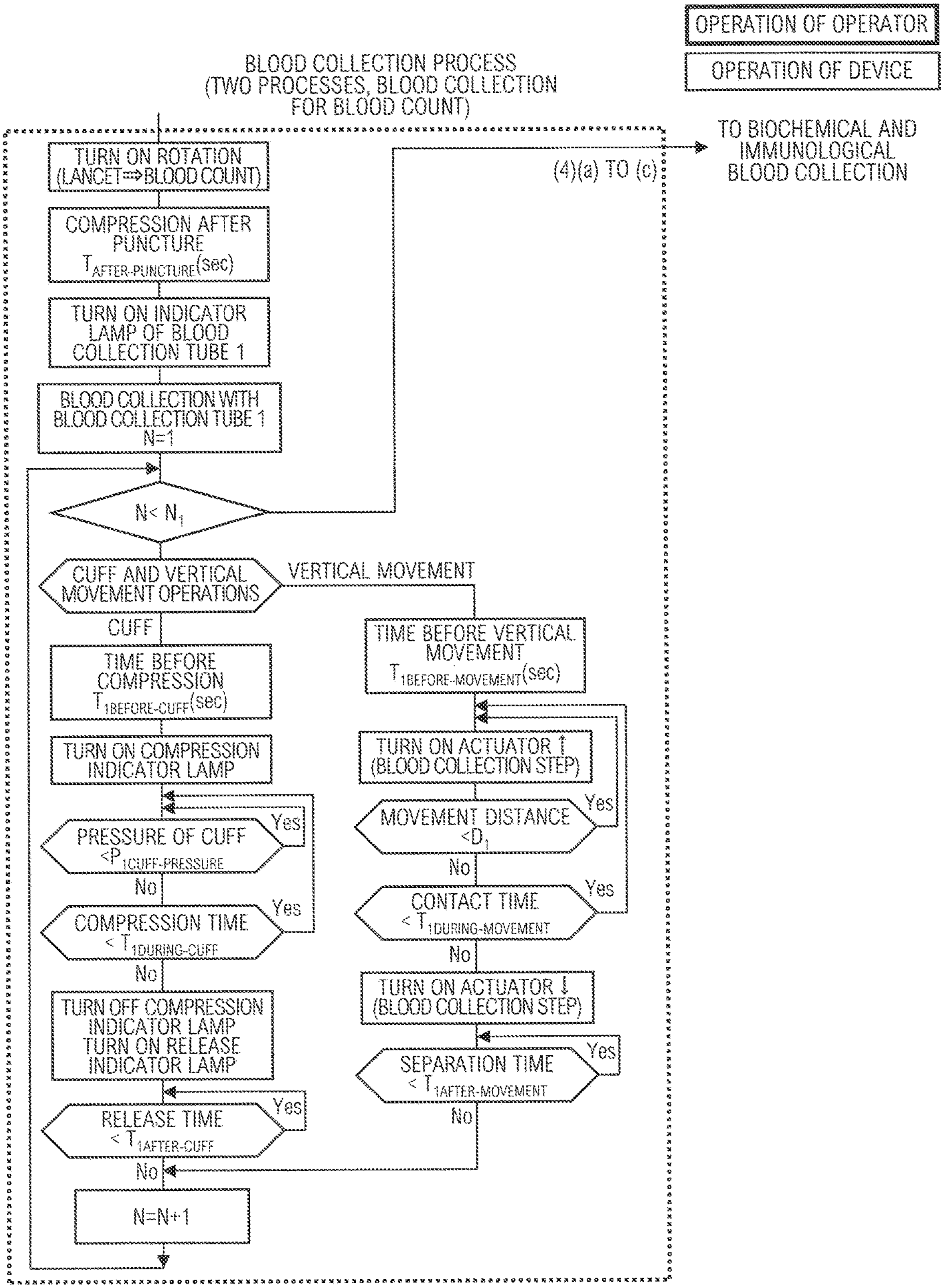
FIG. 6 is a flowchart of the blood collection process by the blood collection apparatus according to the embodiment of the present invention.
Figure 7:
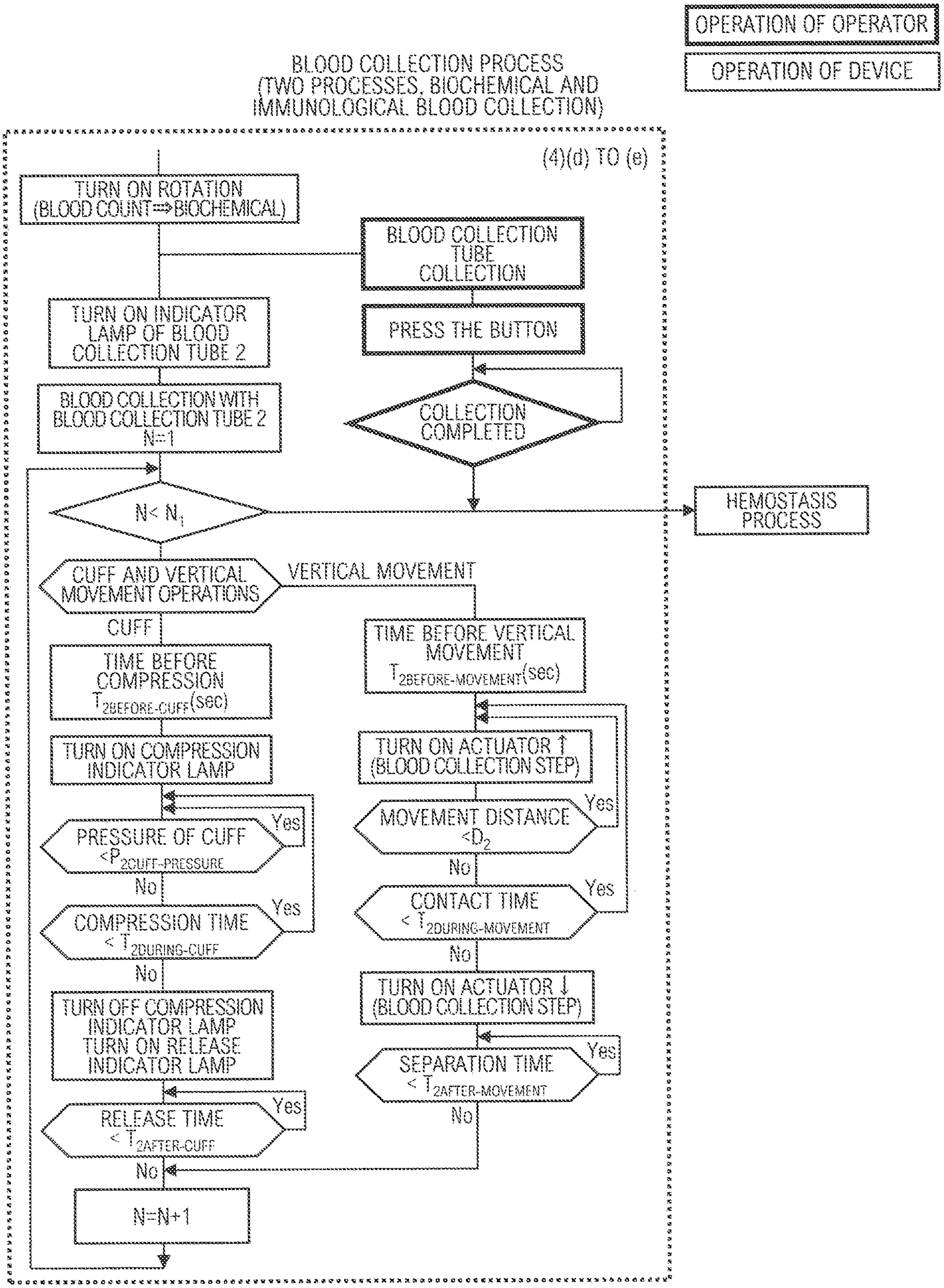
FIG. 7 is a flowchart of the blood collection process by the blood collection apparatus according to the embodiment of the present invention.

Next, a configuration of the cartridge 11 used by the blood collection apparatus 1 according to the embodiment of the present invention will be described with reference to FIG. 3 which is a view of an assembly of the cartridge 11.

The cartridge 11 holds a puncture tool holder 111 that holds the puncture tool 1111, a blood-count blood collection tube holder 112 that holds the blood-count blood collection tube 1121, a blood collection tube holder 113 that holds the biochemical and immunological blood collection tube 1131 that holds the biochemical and immunological blood collection tube 1131, a gauze holder 114 that holds the gauze 1141, and an adhesive bandage holder 115 that holds the adhesive bandage 1151 in a puncture tool holder holding hole 1112, a blood-count blood collection tube holder holding hole 1122, a biochemical and immunological blood collection tube holder holding hole 1132, a gauze holder holding hole (which is hidden by the blood-count blood collection tube holder 112 and thus is not illustrated), and an adhesive bandage holder holding hole 1152 in a cartridge case 110. Centers of the respective holding holes are located on a circumference of a circle about the rotation axis of the cartridge 11. In addition, each of the holding holes is a through hole, but the puncture tool holder 111, the blood-count blood collection tube holder 112, the biochemical and immunological blood collection tube holder 113, the gauze holder 114, and the adhesive bandage holder 115 do not fall from the respective holding holes since a part of each of the puncture tool holder 111, the blood-count blood collection tube holder 112, the biochemical and immunological blood collection tube holder 113, the gauze holder 114, and the adhesive bandage holder 115 is larger than each of the holding holes.

Note that the plurality of blood collection tubes are held in the cartridge 11 in the present embodiment, so that it is possible to collect blood for different purposes of tests by one-time blood collection. In addition, the present embodiment is configured such that the plurality of blood collection tubes of the cartridge 11 can be held on the circumference of the circle about the rotation axis of the cartridge 11, and the plurality of blood collection tubes are arranged at substantially point-symmetric positions about the rotation axis. Thus, for example, there is an effect that another blood collection tube into which blood collection has been completed can be detached during blood collection into one blood collection tube although details will be described later. It is desirable to detach a blood collection tube after blood collection and stir the blood collection tube quickly by inversion and mixing, and thus, it is advantageous that another blood collection tube into which blood collection has been completed can be detached during blood collection into one blood collection tube. These are features that can also be applied to the blood collection apparatus described in PTL 1.

The puncture tool 1111 is a single-use skin puncture tool including a puncture needle and a holder incorporating the puncture needle. When a tip of the puncture tool 1111 is pressed against a finger, the puncture needle protrudes at the moment and punctures a skin and capillary blood vessels of the finger. The blood-count blood collection tube 113 and the biochemical and immunological blood collection tube 114 are containers for collecting blood, and collect blood flowing from a pierced point by pressing mouths of the blood collection tubes against the pierced point of the finger. The blood-count blood collection tube 1121 is a blood collection tube whose inner surface is coated with an anticoagulant, and has an effect of suppressing a coagulation reaction of blood after blood collection. The biochemical and immunological blood collection tube 1131 is a blood collection tube incorporating a separation agent, and can separate blood cells and serum based on a difference in specific gravity by applying a centrifugal force after blood collection. The gauze 1141 is a water-absorbent cloth, and is pressed against the finger to wipe off excess blood from the pierced point of the finger. The adhesive bandage 116 is provided with an absorbent pad at a center of an adhesive sheet, and covers the pierced point of the finger. When being set in the adhesive bandage holder 115, the adhesive bandage 116 is attached with an adhesive surface facing upward.

FIGS. 4 to 9 are flowcharts of a blood collection step of collecting blood from a finger using the blood collection apparatus 1 according to the embodiment of the present invention. The flowchart describes figure numbers corresponding to the respective steps. Blood collection by the blood collection apparatus 1 is performed in the order of (1) an operation check process, (2) a finger setting process, (3) a puncture process, (4) a blood collection process, and (5) a hemostasis process. The blood collection apparatus 1 can be operated directly by a subject or by a person other than the subject. The blood collection step of the blood collection apparatus 1 will be described along the flowcharts of FIGS. 4 to 9. In the drawings, a block with a thick line frame indicates an operation of an operator, and a block with a thin line frame indicates an operation of the apparatus.

(1) Operation Check Process (a) First, when the apparatus is powered on, the rotational-direction driving mechanism 120 (FIG. 2) and the vertical-direction driving mechanism 121 (FIG. 2) operate, and the operation of each of the driving mechanisms is checked. The operation is stopped if there is an abnormality in the operation check, and the processing transitions to cartridge setting if there is no abnormality.

(b) The cartridge 11 is set in the cartridge holder 122 inside the cartridge container 101. After setting the cartridge 11, the processing transitions to cartridge check.

(c) It is checked whether the rotational-direction driving mechanism 120 (FIG. 2) and the vertical-direction driving mechanism 121 (FIG. 2) operate, and the puncture tool holder 111 (FIG. 3), the blood-count blood collection tube holder 112 (FIG. 3), the biochemical and immunological blood collection tube holder 113 (FIG. 3), the gauze holder 114 (FIG. 3), and the adhesive bandage holder 115 (FIG. 3) of the cartridge 11 operate without any abnormality. If there is no abnormality in the operation of the cartridge 11, the processing transitions to input of an ID of a user.

(d) The user of the apparatus inputs the ID of a blood collection subject using the input/output device. Blood collection conditions differ for individual blood collection subjects, and the blood collection condition is input using the input/output device in a case where the blood collection condition of the blood collection subject is not recorded in a memory of the apparatus or in a case of changing the blood collection condition. The blood collection conditions in the present embodiment are set as follows. After the input is finished, the processing transitions to the finger setting process.

(i) Types of Blood Collection Tube

Blood-count blood collection tube and biochemical and immunological blood collection tube.

(ii) Conditions at the Time of Puncture

Figure 10:
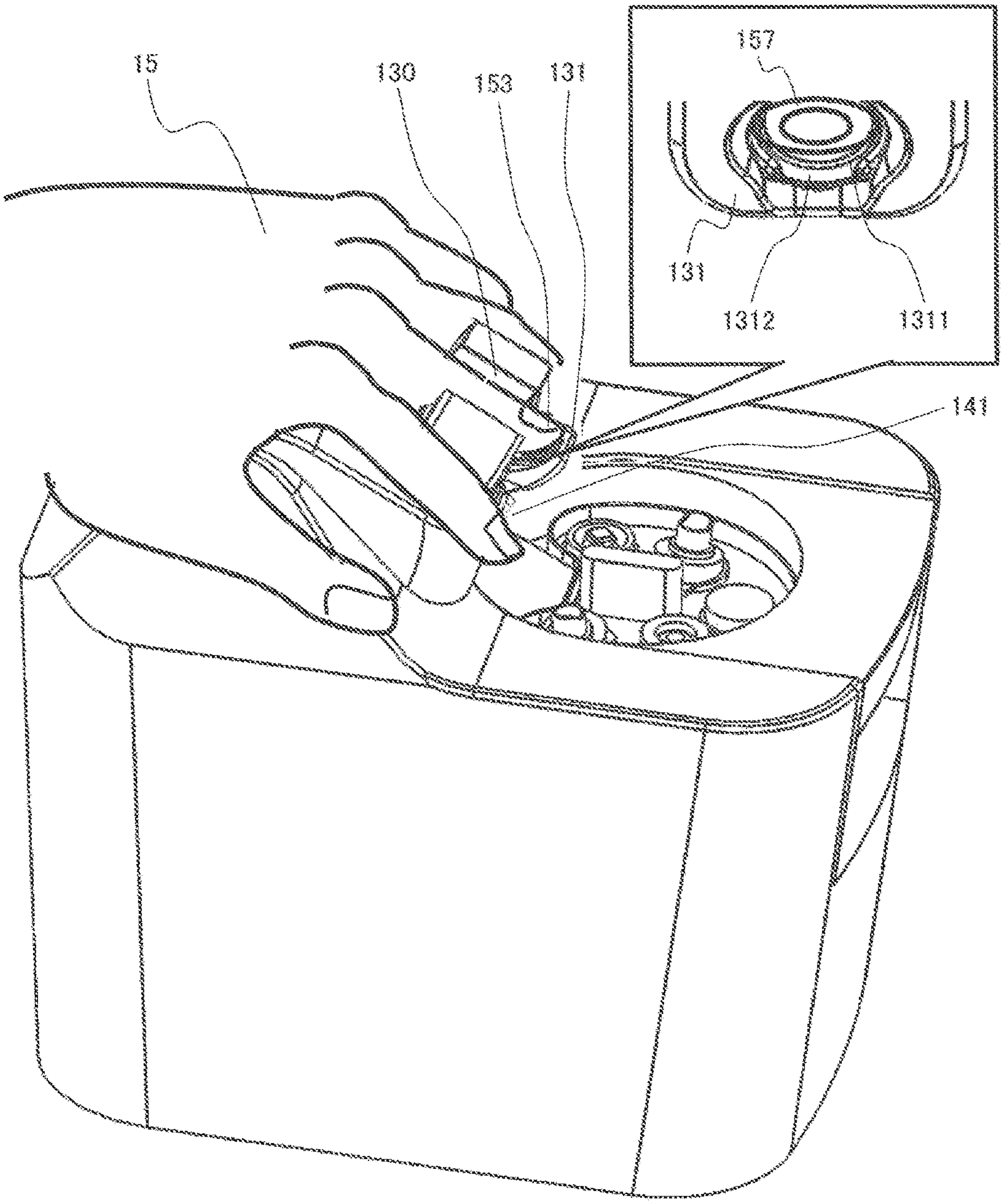
FIG. 10 is a view illustrating a method of fixing a finger to the blood collection apparatus according to the embodiment of the present invention.
Figure 11:
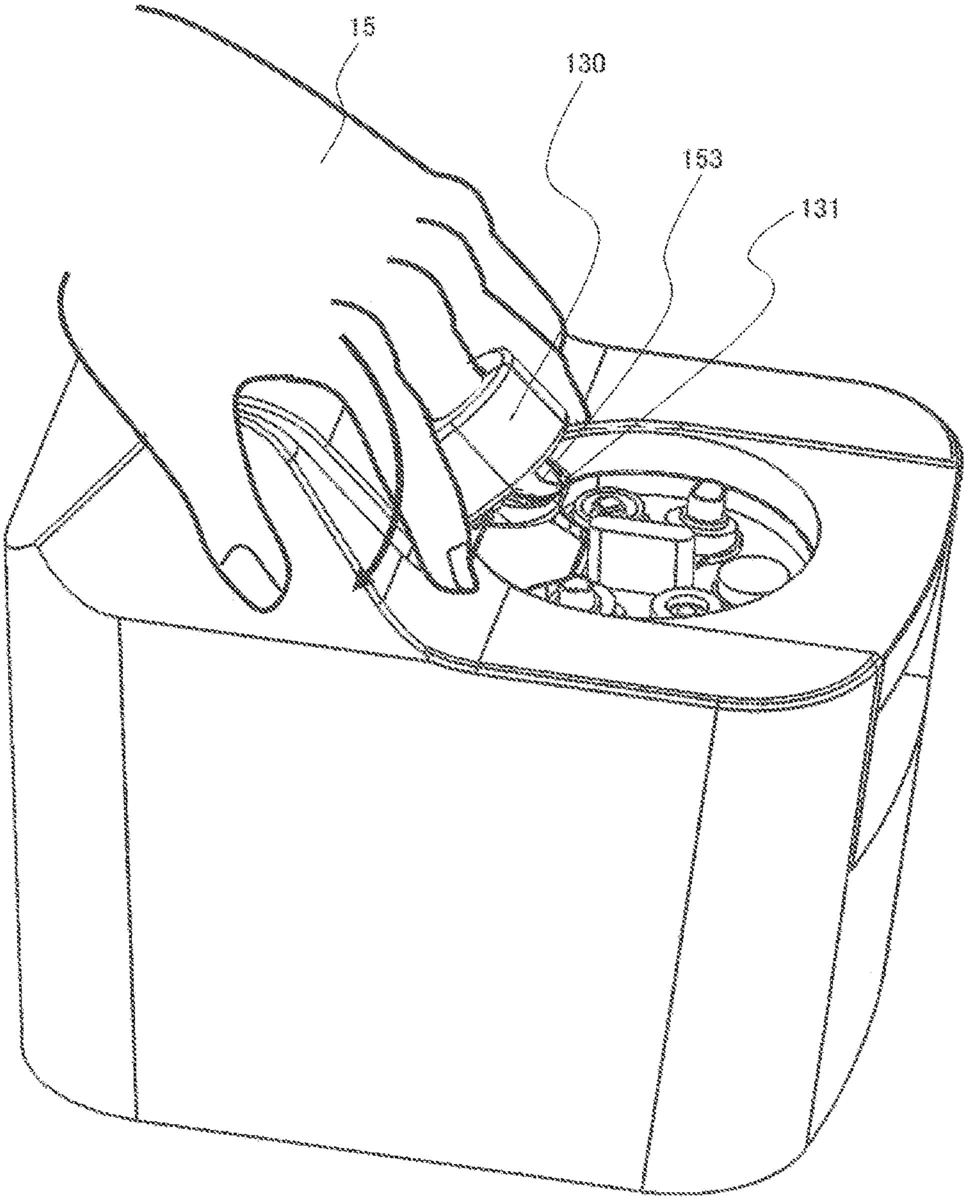
FIG. 11 is a view illustrating the method of fixing the finger to the blood collection apparatus according to the embodiment of the present invention.

Compression time by the cuff before and after puncture: $T_{before\text{-}puncture}$, $T_{after\text{-}puncture}$, Cuff pressure at that time: $P_{puncture}$ (iii) Conditions at the Time of Blood Collection The number of repetitions of compression and release of the cuff at time of blood collection in the blood-count blood collection tube: $N_1$, Standby time before cuff compression: $T_{1before\text{-}cuff}$, Cuff compression time: $T_{1during\text{-}cuff}$, Cuff release time: $T_{1after\text{-}cuff}$, Cuff pressure: $P_{1cuff\text{-}pressure}$ The number of repetitions of compression and release of the cuff at the time of blood collection in the biochemical and immunological blood collection tube: $N_2$, Standby time before cuff compression: $T_{2before\text{-}cuff}$, Cuff compression time: $T_{2during\text{-}cuff}$, Cuff release time: $T_{2after\text{-}cuff}$, Cuff pressure: $P_{2cuff\text{-}pressure}$ (2) Finger Setting Process (a) FIGS. 10 and 11 illustrate a procedure of fixing the middle finger 153 to the blood collection apparatus 1. In the present embodiment, blood is collected from the middle finger, but the blood collection target finger may be a ring finger or an index finger. First, a finger tip of the middle finger 153 is placed on the finger placement portion 131 (FIG. 11). At this time, confirmation is performed with the camera 141 for finger tip confirmation in order to confirm a position where the finger tip is placed. The camera for finger tip confirmation is arranged so as to look into the finger placement portion 131 from below, and it is possible to see the finger placement plate component 1312 and the blood collection window 1311 in addition to the finger placement portion 131 as illustrated in a balloon picture of FIG. 10. A result of the setting is confirmed from the position of the finger tip seen from the blood collection window 1311. In addition, it is also possible to more accurately adjust the position by attaching a tape 157 having a ring shape to the finger tip in advance and aligning a center of the ring of the tape 157 with a center of the blood collection window 1311. Although the position of the finger tip is visually confirmed in the present embodiment, automation by an image recognition technology is also possible.

(b) After the setting of the finger tip is completed, the cuff mechanism fixing unit 13 is pushed in a direction of an arrow in the drawing as illustrated in FIG. 11. The cuff mechanism 130 is closed by a mechanical mechanism by pushing the cuff mechanism fixing unit 13 (FIG. 1) so that the cuff covers the middle finger 153. As a position of the cuff mechanism fixing unit 13 is changed, a height difference among the finger tip of a hand 15, the back of a hand, and a wrist increases, and the amount of blood flowing from the finger tip during blood collection can be increased. That is, the cuff mechanism finger fixing unit 13, which is the puncture site holding mechanism, holds the back of the hand on the apparatus at a position higher than the finger tip such that the finger tip is lower than the other sites of the hand in the present embodiment. This feature can also be applied to, for example, the blood collection apparatus described in PTL 1.

After the finger setting process is completed, the operator gives an instruction to start via the input/output device, so that the blood collection apparatus 1 transitions to the puncture process.

Figure 12:
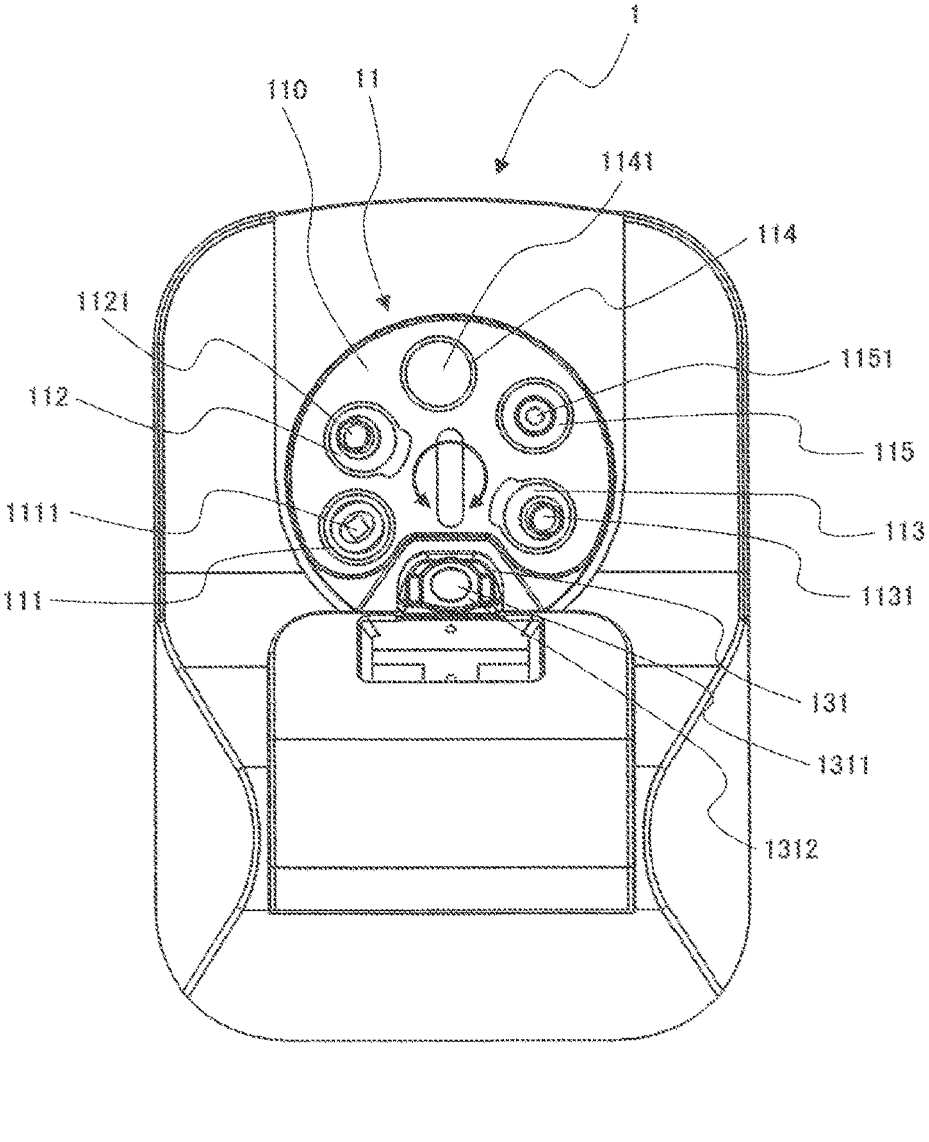
FIG. 12 is a view illustrating a positional relationship between the finger and the cartridge in the blood collection apparatus according to the embodiment of the present invention.

(3) Puncture Process (a) FIG. 12 is a top view of the blood collection apparatus 1, and illustrates a positional relationship among the blood collection window 1311, the cartridge 11, and the puncture tool 1111, the blood-count blood collection tube 1121, the biochemical/immune blood collection tube 1131, the gauze 114, and the adhesive bandage 115 constituting the cartridge 11. The cartridge 11 is rotated in a direction of an arrow in the drawing by the rotational-direction driving mechanism 120 (FIG. 2). Through the rotation, the puncture tool 1111, the blood-count blood collection tube 1121, the biochemical/immune blood collection tube 1131, the gauze 114, and the adhesive bandage 115 can be arranged immediately below the blood collection window 1311.

(b) First, the internal pressure of the cuff is increased by the pressure adjustment mechanism (not illustrated), the finger tip of the middle finger 153 as the blood collection target is compressed so that blood is collected on the finger tip. Note that more blood can be collected on the finger tip by compressing a range from the first joint of the finger where the capillary vessels are densely packed to the finger tip than by compressing a range from the first joint to the root of the finger, and thus, such a range is suitable as a compressing range.

Figure 13:
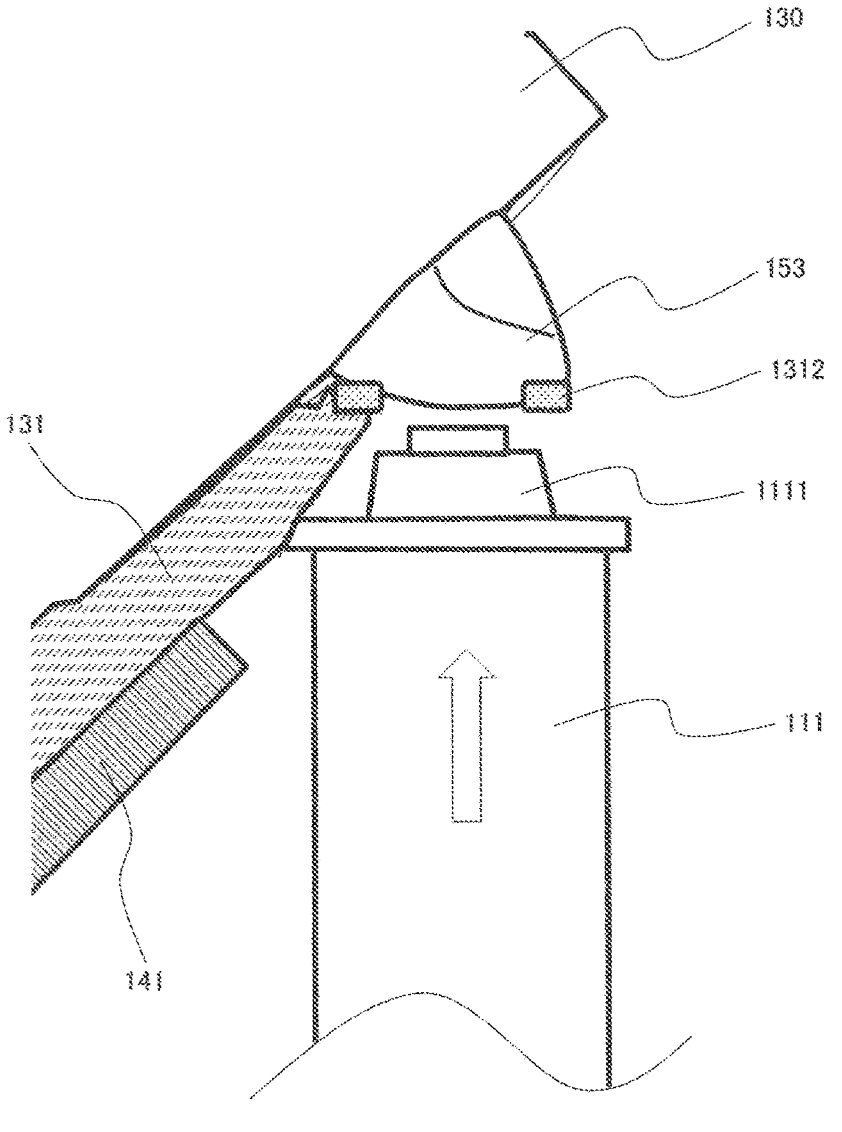
FIG. 13 is a view illustrating a positional relationship between the finger and a puncture tool in the blood collection apparatus according to the embodiment of the present invention.

(c) In parallel with the compression with the cuff, the rotational-direction driving mechanism 120 (FIG. 2) rotates the cartridge 11 to move the puncture tool 1111 immediately below the blood collection window 1311. FIG. 13 is a view illustrating a positional relationship between the middle finger 153 and the puncture tool 1111 immediately before puncture. During compression of the finger tip, the puncture tool holder 111 is pushed up toward the finger tip of the middle finger 153 by the vertical-direction driving mechanism 121 (FIG. 2), and the finger tip is punctured by pressing the puncture tool 1111 against the middle finger 153.

After the puncture process is completed, the processing transitions to the blood collection process.

(4) Blood Collection Process (a) The blood collection process is divided into a blood collection process collecting two (blood count and biochemical and immunological) blood collection tubes and a blood collection process collecting one (blood count or biochemical and immunological) blood collection tube depending on the conditions of the blood tube pipe input in the operation check process. In the present embodiment, a case where the collection of two blood collection tubes will be described.

The cartridge 11 is rotated by the rotational-direction driving mechanism 120 (FIG. 2) to move the blood-count blood collection tube 1121 immediately below the blood collection window 1311. Subsequently, the blood-count blood collection tube holder 112 is pushed up toward the finger tip of the middle finger 153 by the vertical-direction driving mechanism 121, and the mouth of the blood-count blood collection tube 1121 is brought close to the middle finger 153. When blood flowing from a puncture point of the finger tip touches the mouth of the blood-count blood collection tube 1121, the blood enters the blood-count blood collection tube 1121 due to the wettability of the mouth of the blood-count blood collection tube 1121.

Figure 14:
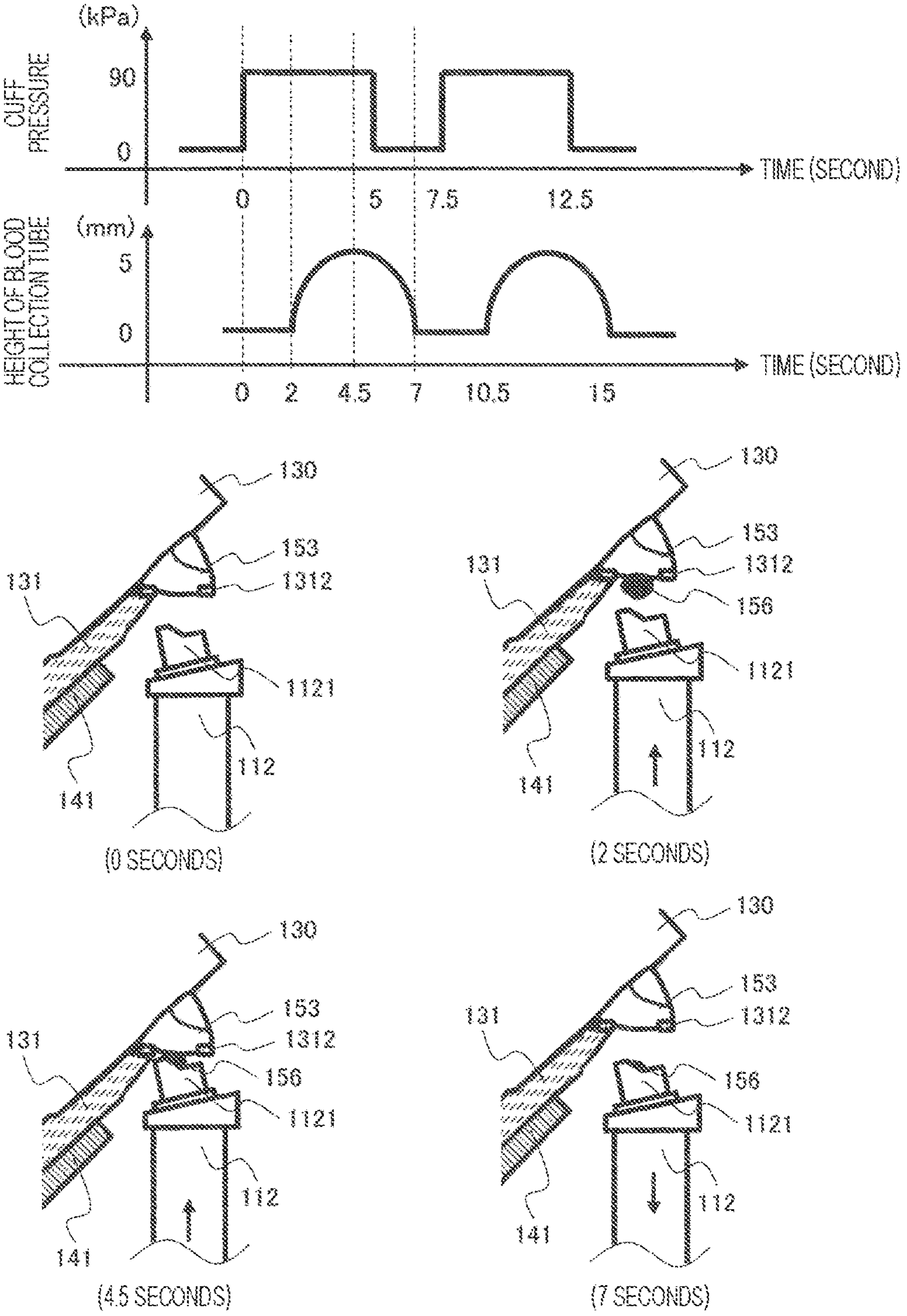
FIG. 14 is a view illustrating a positional relationship between the finger and a blood collection tube and a pressure change of a cuff in the blood collection apparatus according to the embodiment of the present invention.

(b) A method of compressing a finger tip and a method of operating a blood collection tube having an effect of increasing the blood collection amount will be described with reference to FIG. 14. FIG. 14 illustrates temporal changes in the internal pressure of the cuff and the position of the blood-count blood collection tube at the time of blood collection, and positional relationships between the finger tip and the blood-count blood collection tube 1121 and states of blood from the finger tip at four time points.

The internal pressure of the cuff changes at a cycle of 7.5 sec. including 5 sec. (at the time of compression) of 90 kPa and 2.5 sec. (at the time of release) of 0 kPa. Meanwhile, the blood collection tube also changes in the vertical movement of 5 mm at a cycle of 7 sec. The pressure here is a differential pressure from atmospheric pressure.

Although there is little blood flowing from the finger tip immediately after the finger tip is compressed (at a time point of 0 sec.), the blood is collected on the finger tip by compressing the finger tip with the cuff, and the blood flowing from the puncture point forms a droplet on the finger tip (at a time point of 2 sec.). As the compression with the cuff is continued, the droplet of the blood becomes larger.

Immediately before the end of the cuff compression, the mouth of the blood-count blood collection tube 1121 is brought close to the finger tip, and the droplet of blood is brought into contact with the blood-count blood collection tube 1121 (at a time point of 4.5 sec.). As a result of the contact, a part of the droplet of blood drops on a bottom of the blood-count blood collection tube 1121, and a part of the blood remains between the finger tip and the mouth of the blood-count blood collection tube 1121.

After the contact, the finger tip is released from the compression by adjusting the internal pressure of the cuff to 0 kPa. This operation opens a blood vessel of the tightened finger, so that blood flows to the finger tip again. Subsequently, the mouth of the blood-count blood collection tube 1121 is separated from the finger tip. With this operation, the blood accumulated between the finger tip and the mouth of the blood-count blood collection tube 1121 can be separated toward the mouth of the blood-count blood collection tube 1121 (at a time point of 7 sec.). The separated blood moves toward the bottom of the blood-count blood collection tube 1121 by gravity. In this manner, blood is collected in the blood-count blood collection tube 1121 by repeating the compression and release of the cuff and the change of the relative distance between the finger tip and the blood-count blood collection tube 1121.

Since the compression and release with the cuff are repeated, it is possible to repeat promotion of bleeding from the finger tip and replenishment of blood to the finger tip. In addition, in a case where it is difficult to change the distance between the blood-count blood collection tube 1121 and the finger tip, the coagulation reaction proceeds in the blood accumulated between the finger tip and the mouth of the blood-count blood collection tube 1121 so that bleeding from the puncture point is delayed. However, the coagulation reaction at the puncture point can be suppressed by changing the distance between the blood-count blood collection tube 1121 and the finger tip and removing the blood accumulated between the finger tip and the mouth of the blood-count blood collection tube 1121 at regular time intervals as in the present embodiment. As a result, the effect of increasing the blood collection amount can be obtained by repeating the compression and release with the cuff and the change of the distance between the blood-count blood collection tube 1121 and the finger tip. In the present embodiment, the compression and release of the cuff is performed at the cycle of 7.5 sec. including 5 sec. and 2.5 sec., and the vertical movement of the blood-count blood collection tube 1121 is also performed at the cycle of 7.5 sec. with the amplitude of 5 mm. However, it is preferable to change these conditions depending on a state of a blood collection subject. These conditions are determined based on results of blood collection from subjects in various states. For example, in a case of a subject with thick fingers, conditions are generally set with a shorter cycle than that of a subject with thin fingers. Further, the relative distance between the finger tip and the blood-count blood collection tube 1121 is changed by moving the blood-count blood collection tube 1121 in the present embodiment, but a similar effect can be expected even if the relative distance between the finger tip and the blood-count blood collection tube 1121 is changed by fixing the blood-count blood collection tube 1121 and moving the finger tip. In addition, a similar effect can be expected even if the cartridge itself is vertically moved to change the relative distance between the finger tip and the blood-count blood collection tube 1121. In addition, it is preferable that a repetition timing of the compression and release of the finger tip with the cuff and a repetition timing of the change of the relative distance between the finger tip and the blood-count blood collection tube 1121 be set such that the blood-count blood collection tube 1121 is brought close to the finger tip immediately before the end of the compression of the cuff and the blood-count blood collection tube 1121 is separated from the finger tip after the release of the cuff as illustrated in FIG. 14, but the present invention is not necessarily limited thereto. It is important to remove the blood accumulated between the finger tip and the mouth of the blood-count blood collection tube 1121 at predetermined time intervals, and it is possible to suppress the coagulation of the blood at the puncture point and to expect the increase in the blood collection amount by repeatedly changing the relative distance between the finger tip and the blood-count blood collection tube 1121 at predetermined time intervals during the blood collection by the compression and release of the cuff.

Figure 15:
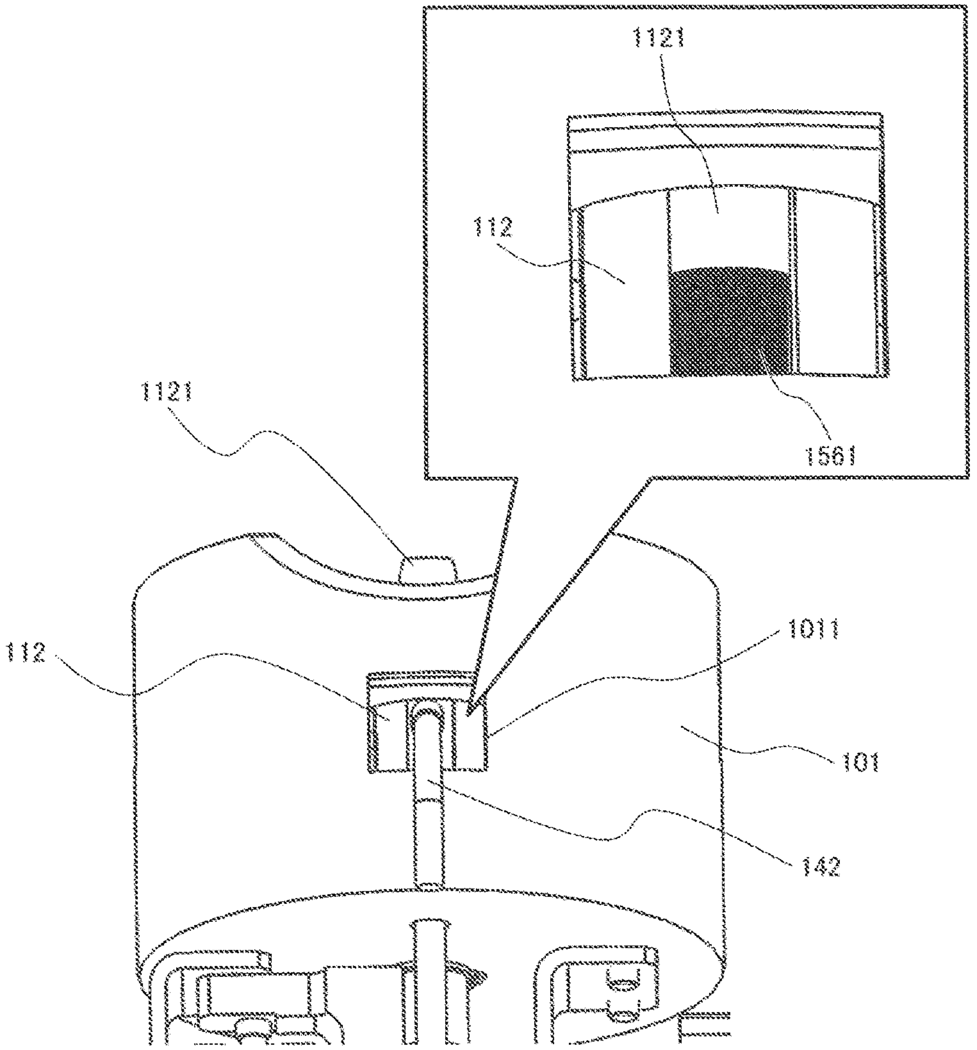
FIG. 15 is a view illustrating a positional relationship between a blood collection amount observation camera and the blood collection tube in the blood collection apparatus according to the embodiment of the present invention.

(c) The blood collection amount in the blood-count blood collection tube 1121 is measured by the camera 142 for blood collection amount confirmation (FIG. 2). FIG. 15 is a view of the cartridge container 101 (FIG. 1) when blood is collected in the blood-count blood collection tube 1121 as viewed from the side of the camera 142 for blood collection amount confirmation (FIG. 2). The cartridge container 101 has a blood collection amount observation window 1011 which is a void, and the blood-count blood collection tube holder 112 holding the blood-count blood collection tube 1121 also has a void. When blood is collected in the blood-count blood collection tube 1121, blood 1561 collected in the blood-count blood collection tube 1121 can be observed through these voids. Through visual observation or image analysis, the blood collection into the blood-count blood collection tube 1121 is ended at a stage where a predetermined blood collection amount is obtained, and the processing transitions to blood collection into the biochemical and immunological blood collection tube 1131.

(d) The cartridge 11 is rotated by the rotational-direction driving mechanism 120 (FIG. 2) to move the biochemical and immunological blood collection tube 1131 immediately below the blood collection window 1311. The blood collection into the biochemical and immunological blood collection tube 1131 is performed by a similar operation as that in the blood collection into the blood-count blood collection tube 1121.

Figure 16:
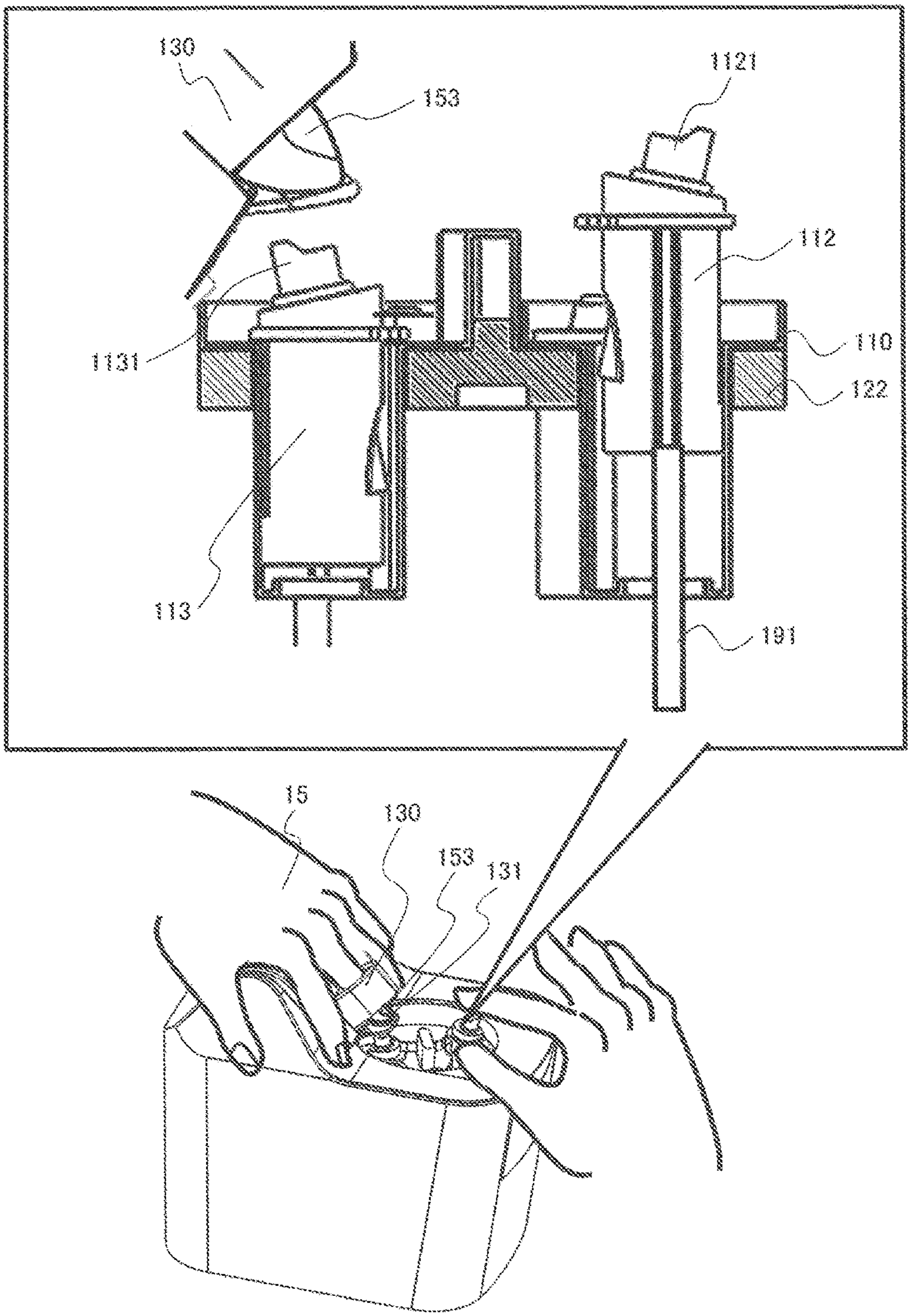
FIG. 16 is a view illustrating a positional relationship between the finger and the blood collection tube in the blood collection apparatus according to the embodiment of the present invention.

(e) In addition, the blood-count blood collection tube 1121 into which blood collection has been completed is detached and subjected to inversion and mixing during blood collection into the biochemical and immunological blood collection tube 1131 since the coagulation reaction proceeds in the blood collected by the blood-count blood collection tube 1121. Through the inversion and mixing, the anticoagulant attached to the inner surface of the blood-count blood collection tube 1121 is mixed with the blood so that the coagulation reaction is suppressed. FIG. 16 is a view illustrating how to detach the blood-count blood collection tube 1121. Since the blood-count blood collection tube 1121 and the biochemical and immunological blood collection tube 1131 are arranged to be point-symmetric with respect to the center of the cartridge 11 (FIG. 3), the blood-count blood collection tube 1121 is located at the farthest position from the finger tip during the blood collection into the biochemical and immunological blood collection tube 1131. When the blood-count blood collection tube 1121 at such a position is moved upward with a blood collection tube detachment rod 191, the blood-count blood collection tube 1121 can be detached.

After the blood collection into the biochemical and immunological blood collection tube 1131 is completed, the processing transitions to the hemostasis process.

(5) Hemostasis Process (a) The cartridge 11 is rotated by the rotational-direction driving mechanism 120 (FIG. 2) to move the gauze 1141 immediately below the blood collection window 1311. Subsequently, the gauze 1141 is pushed up toward the finger tip of the middle finger 153 by the vertical-direction driving mechanism 121, and the gauze 1141 is brought into contact with the finger tip of the middle finger 153 to wipe off the blood remaining on the finger tip.

(b) Thereafter, the cartridge 11 is rotated to move the adhesive bandage 1151 directly below the blood collection window 1311. Subsequently, the adhesive bandage 1151 is pushed up toward the finger tip of the middle finger 153 by the vertical-direction driving mechanism 121, and the adhesive bandage 1151 is pasted to the finger tip of the middle finger 153 to cover the puncture point of the finger tip.

Since the blood remaining on the finger tip is wiped off with the gauze 1141 before covering the puncture point with the adhesive bandage 1151, it is possible to prevent the blood from overflowing from the adhesive bandage 1151 and reliably paste the adhesive bandage 1151 to the finger tip.

(c) After the adhesive bandage 1151 is pasted, the blood collection subject takes off the middle finger 153 from the cuff mechanism. Thereafter, the biochemical and immunological blood collection tube 1131 is detached by a similar method as that of the blood-count blood collection tube 1121.

Figure 8:
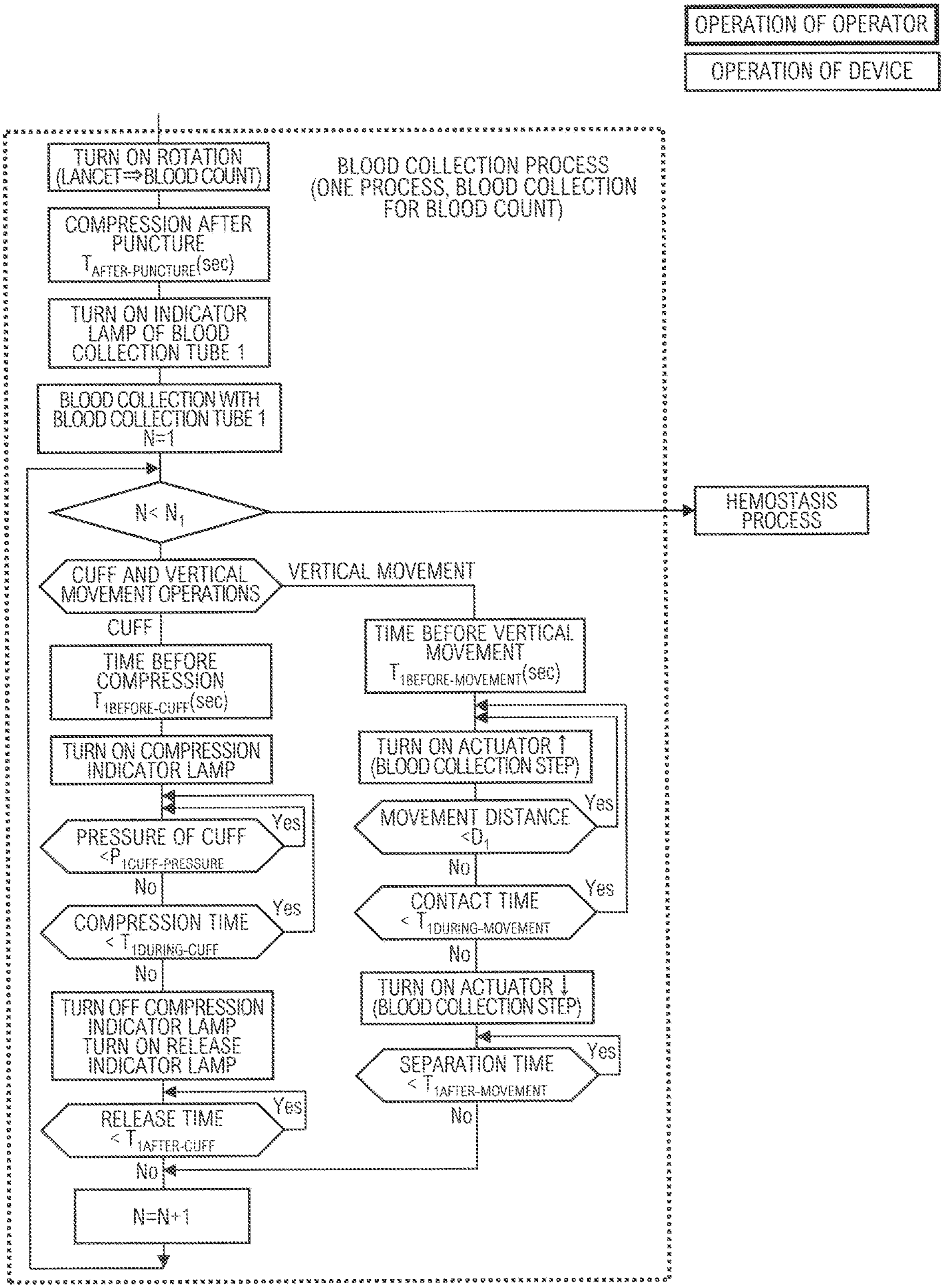
FIG. 8 is a flowchart of the blood collection process by the blood collection apparatus according to the embodiment of the present invention.
Figure 9:
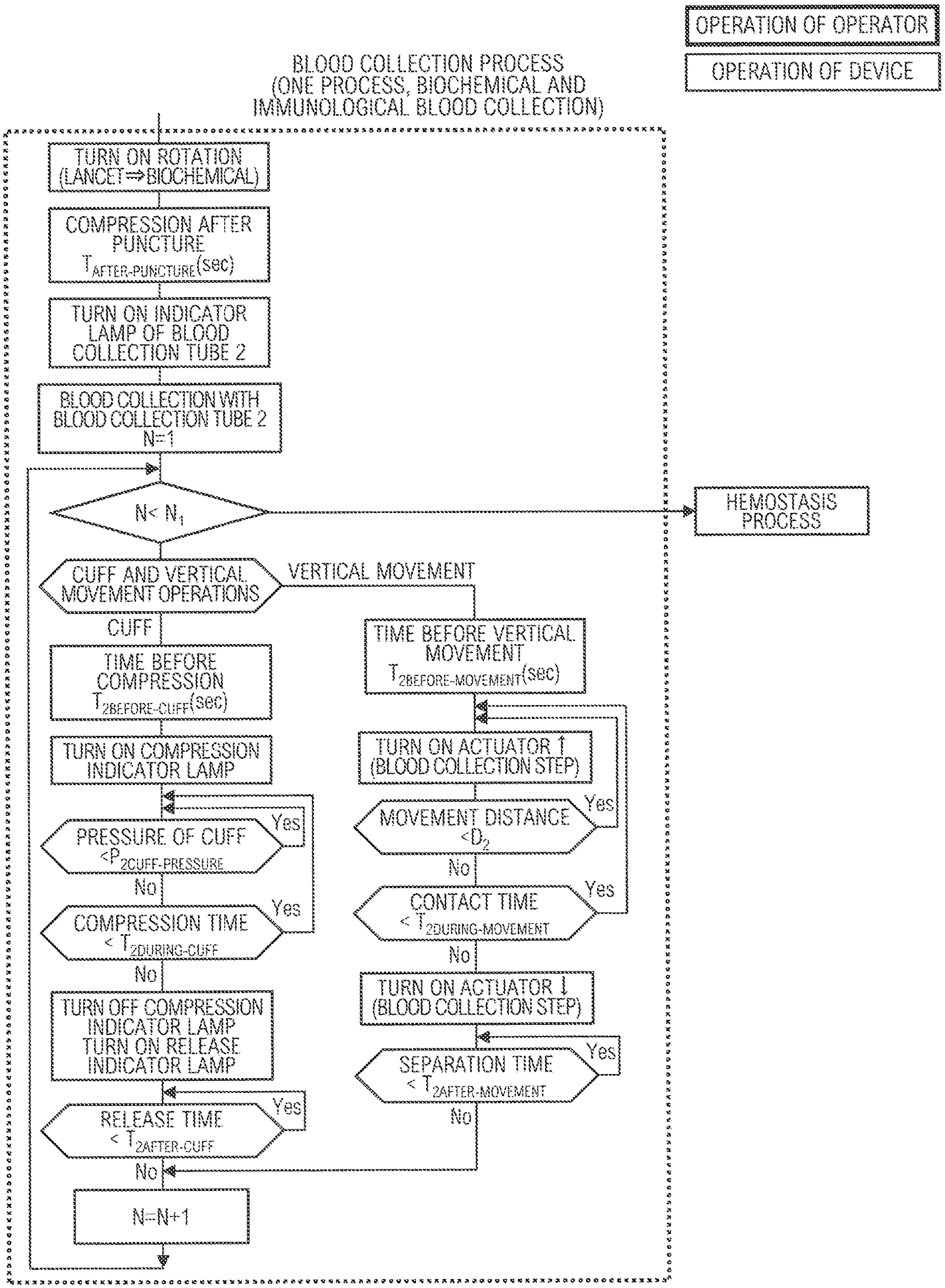
FIG. 9 is a flowchart of the blood collection process by the blood collection apparatus according to the embodiment of the present invention.

According to the above procedure using the blood collection apparatus 1, the blood is collected into the blood-count blood collection tube 1121 and the biochemical and immunological blood collection tube 1131. Although the blood is collected into the two blood collection tubes (the blood-count blood collection tube and the biochemical and immunological blood collection tube) in the present embodiment, only the blood collection into the blood-count blood collection tube 1121 or only the blood collection into the biochemical and immunological blood collection tube 1131 can be also performed according to procedures illustrated in FIGS. 8 and 9. FIG. 8 is a flowchart when only the blood collection into the blood-count blood collection tube is performed, in which the processing transitions to the hemostasis process after the end of the blood collection into the blood-count blood collection tube. FIG. 9 is a flowchart when only the blood collection into the biochemical and immunological blood collection tube is performed, in which the processing transitions to the blood collection process for the biochemical and immunological blood collection tube after the end of the puncture process.

Next, a preferable movement method of the cartridge 11 in blood collection, a preferable shape of a blood collection tube, a method of covering a blood collection tube after blood collection with a lid and stirring the blood collection tube, and a method of performing only the blood collection process will be described.

First, the preferable movement method of the cartridge 11 will be described. In the blood collection by the blood collection apparatus of the present embodiment, there is a possibility that blood may drop from the finger tip after puncture. Therefore, it is preferable to rotate the cartridge 11 so as not to pass over components (the biochemical and immunological blood collection tube 1131, the gauze 1141, and the adhesive bandage 1151) to be used in subsequent steps. Therefore, in the case of using the cartridge 11 of FIG. 12, the cartridge 11 is rotated such that the puncture process→counterclockwise→the blood collection process (blood count)→clockwise→the blood collection process (biochemical and immunological) counterclockwise→the hemostasis process (gauze)→the hemostasis process (adhesive bandage). Note that the rotational direction is different in a case where types or arrangements of components incorporated in the cartridge are different. That is, it is preferable to move the cartridge so as not to pass over the components used in the subsequent steps.

According to the present embodiment, since the blood collection apparatus using the blood collection tube, a finger compression and release mechanism, and a vertical-direction movement mechanism of the blood collection tube is provided, an extremely excellent effect that stable blood collection can be constantly realized for any subject is exhibited.

Figure 17:
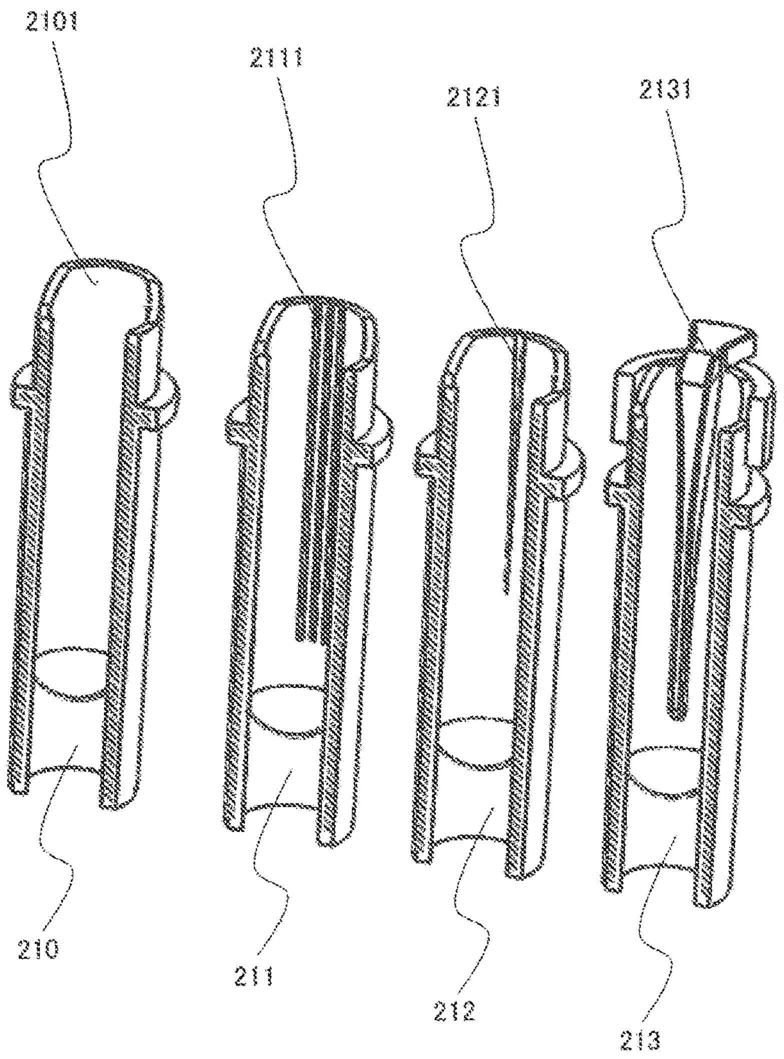
FIG. 17 is a view illustrating a configuration example of the blood collection tube used in the blood collection apparatus according to the embodiment of the present invention.

Next, the preferable shape of the blood collection tube will be described. The blood collection in the present embodiment is characterized in that the droplet of blood is transferred from the finger tip to the blood collection tube by changing the relative distance between the finger tip and the blood collection tube. Therefore, it is desirable that the blood collection tube have performance of attracting blood that is in contact. FIG. 17 is a cross-sectional view of a blood collection tube 210 having the same shape as the blood collection tube used in the present embodiment, and a blood collection tube with grooves 211, a blood collection tube with a tapered groove 212, and a blood collection tube with a blood collection guide 213 having improved performance of attracting blood that is in contact, obtained by improving the wettability of the surface. Specifically, the blood collection tube with grooves 211 has a plurality of thin linear grooves at a mouth 2111, the blood collection tube with a tapered groove 212 has a tapered groove at a mouth 2121 (a groove having a wider groove width on the inlet side and a narrower groove width toward the lower side), and the blood collection tube with a blood collection guide 213 has a tapered guide at a mouth 2131 (a protruding guide having a wider width on the inlet side and a narrower groove width toward the lower side), thereby increasing the wettability. The number of grooves or guides may be one or more. The protruding guide may be linear.

Next, automation of covering a blood collection tube after blood collection with a lid and stirring will be described. Although the blood collection tube after blood collection is detached and stirred by inversion and mixing in the above-described embodiment, the blood collection tube can be automatically covered with the lid and stirred in the apparatus by adding the following mechanism in the apparatus.

Figure 18A:
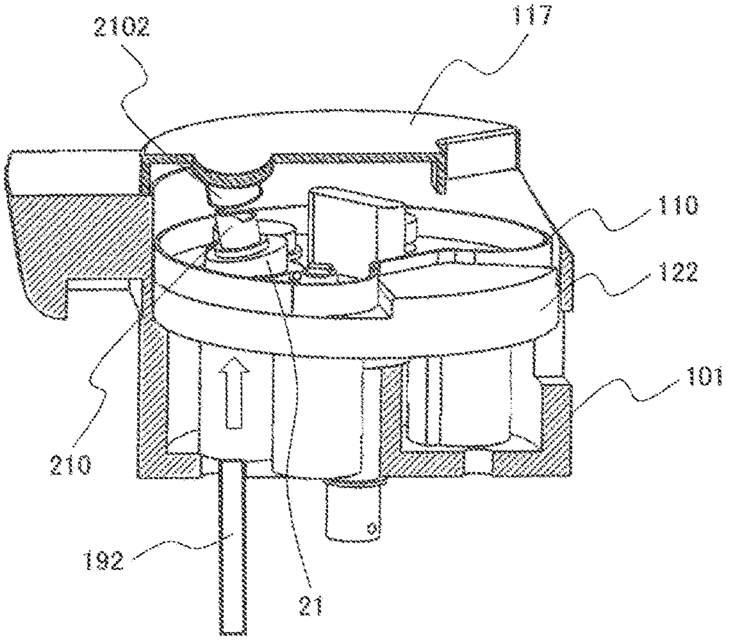
FIG. 18A is a view illustrating a method of attaching a lid to the blood collection tube in the blood collection apparatus according to the embodiment of the present invention, and illustrating a state before the lid is attached.
Figure 18B:
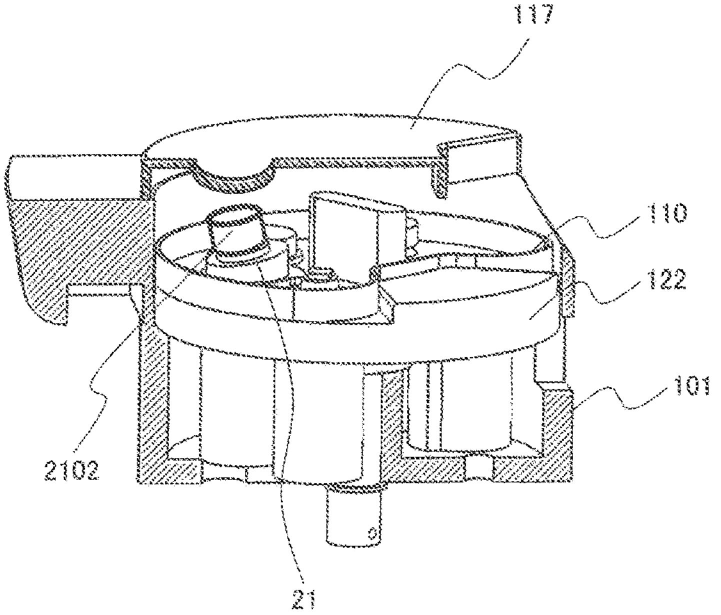
FIG. 18B is a view illustrating the method of attaching the lid to the blood collection tube in the blood collection apparatus according to the embodiment of the present invention, and illustrating a state after the lid is attached.

FIGS. 18A and 18B are views illustrating an operation for attaching a blood collection tube lid 2102 to the blood collection tube 210 in the cartridge container 101, and illustrate the cartridge container 101 and a cover 117 in a cross-sectional view. When the cover 117 holding the blood collection tube lid 2102 is arranged above the cartridge 11 (FIG. 18A), the blood collection tube 210 can be covered with the blood collection tube lid 2102 by pushing the blood collection tube 210 into which blood collection has been completed upward by a lid attachment rod 192 to be pushed into the blood collection tube lid 2102 (FIG. 18B).

Figure 19:
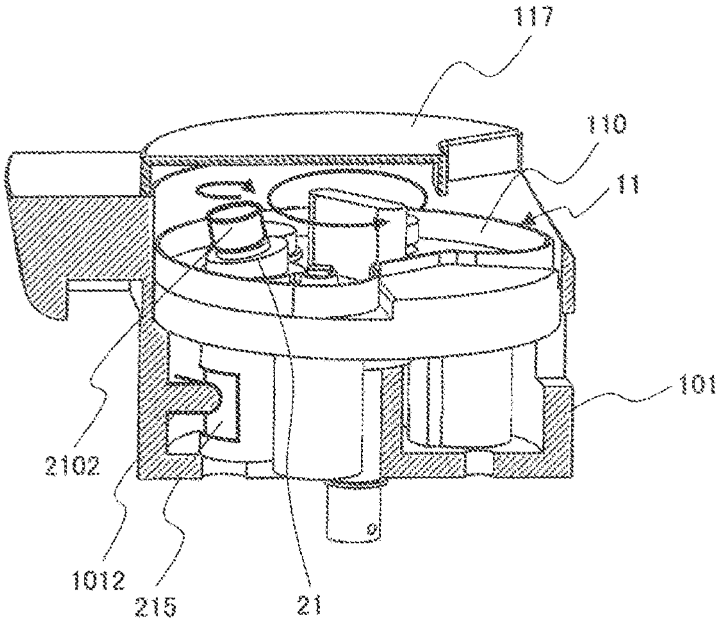
FIG. 19 is a view illustrating an example of a method of stirring the blood collection tube in the blood collection apparatus according to the embodiment of the present invention.

FIG. 19 is a view illustrating an operation for rotation, revolution, and stirring of blood in the blood collection tube 210 inside the cartridge container 101, and illustrates the cartridge container 101 and the cover 117 in a cross-sectional view similarly to FIGS. 18A and 18B. When a protrusion 1012 is provided in the cartridge container 101, a gap 215 is provided in a portion of the cartridge case 110 that holds a blood collection tube holder 21, and the cartridge 11 is rotated (counterclockwise in the drawing) by the rotational-direction driving mechanism 120 in this state, the blood collection tube holder 21 receives a force clockwise by the protrusion 1012. With this force, the blood collection tube holder 21 performs a planetary motion of revolving while rotating so that it is possible to rotate, revolve, and stir the blood in the blood collection tube 210.

Although all the steps of puncture, blood collection, and hemostasis are performed using the blood collection apparatus 1 in the present embodiment, one of features of the present invention is the increase in the blood collection amount during the blood collection. Therefore, the puncture and hemostasis may be performed manually.

In such a case, a finger is punctured with a commercially available puncture tool, and then, the finger is set in the blood collection apparatus 1 in which the cartridge 11 attached with only a holder for holding a blood collection tube is set in advance. Thereafter, only the above-described blood collection process is performed, and then, the finger is taken off from the blood collection apparatus 1 to manually perform hemostasis. It can be expected to obtain a larger blood collection amount by using the blood collection apparatus of the present embodiment as compared with a case where blood collection is manually performed.

REFERENCE SIGNS LIST

1 blood collection apparatus
11 cartridge
12 driving mechanism
13 cuff mechanism finger fixing unit
15 hand
16 control mechanism
17 pressure adjustment mechanism
100 case
101 cartridge container
110 cartridge case
111 puncture tool holder
112 blood-count blood collection tube holder
113 biochemical and immunological blood collection tube holder
114 gauze holder
115 adhesive bandage holder
120 rotational-direction driving mechanism
121 vertical-direction driving mechanism
122 cartridge holder
141 finger tip confirmation camera
142 blood collection amount confirmation camera
153 finger
171 cuff internal pressure sensor
172 cuff valve
173 cuff pump
191 blood collection tube detachment rod
192 lid attachment rod
210 blood collection tube
211 blood collection tube with grooves
212 blood collection tube with tapered groove
213 blood collection tube with blood collection guide
1111 puncture tool
1121 blood-count blood collection tube
1131 biochemical and immunological blood collection tube
1141 gauze
1151 adhesive bandage
1311 blood collection window
1312 finger placement plate component.

The invention claimed is:

1. A blood collection apparatus comprising:

a puncture site holding mechanism for holding a puncture site of a subject;

a compression mechanism for performing an operation of compressing and releasing the puncture site when the blood is collected from the puncture site;

a container holding mechanism for holding a container for collecting blood flowing from a puncture wound at the puncture site; and a driving mechanism configured to:

vary a relative distance between the puncture site and the container by vertically moving the puncture site holding mechanism, the container holding mechanism, or the container held by the container holding mechanism while the compression mechanism performs the operation of compressing and releasing the puncture site, and repeatedly vary the relative distance between the puncture site and the container by vertically moving the puncture site holding mechanism, the container holding mechanism, or the container held by the container holding mechanism while the compression mechanism performs the operation of compressing and releasing the puncture site.

2. The blood collection apparatus according to claim 1, wherein the driving mechanism vertically moves the container to vary a relative distance between the puncture site and the container.

3. The blood collection apparatus according to claim 1, wherein the driving mechanism vertically moves the puncture site holding mechanism to vary a relative distance between the puncture site and the container.

4. The blood collection apparatus according to claim 2, wherein the compression mechanism and the driving mechanism perform the operation of compressing and releasing the puncture site and the vertical movement of the container based on an operation content input by an apparatus operator.

5. The blood collection apparatus according to claim 4, wherein the compression mechanism and the driving mechanism periodically perform the operation of compressing and releasing the puncture site and the vertical movement of the container.

6. The blood collection apparatus according to claim 5, wherein the compression mechanism and the driving mechanism perform the operation of compressing and releasing the puncture site and vertical movement of the container in a predetermined relationship.

7. The blood collection apparatus according to claim 2, wherein the container holding mechanism includes a puncture tool that punctures the puncture site, a gauze that comes into contact with the puncture wound, and a mechanism for holding a seal that seals the puncture wound, and wherein the driving mechanism includes a horizontal-direction driving mechanism that changes a relative position between the puncture site and the puncture tool, the container, the gauze, or the seal on a horizontal plane, and a vertical-direction driving mechanism that changes a relative position between the puncture site and the puncture tool, the container, the gauze, or the seal in a vertical direction.

8. The blood collection apparatus according to claim 7, wherein the container holding mechanism has a part made of a transparent substance or a void such that contents of the container is measurable from an outside of the container holding mechanism by an optical method.

9. The blood collection apparatus according to claim 8, wherein the puncture tool, the container, the gauze, and the seal are arranged on a circumference about a vertical axis passing through the container holding mechanism.

10. The blood collection apparatus according to claim 9, wherein the container holding mechanism changes the relative position between the puncture site and the puncture tool, the container, the gauze, or the seal on the horizontal plane by performing a rotational motion about the vertical axis, and passes immediately below a planned puncture point of the puncture site in an order of the puncture tool, the container, the gauze, and the seal during the rotational motion.

11. The blood collection apparatus according to claim 10, wherein the container holding mechanism holds two containers, each of which serves as the container, and the two containers are located at positions facing each other with respect to the vertical axis.

12. The blood collection apparatus according to claim 11, further comprising:

a component which is separably attached to the puncture site holding mechanism and on which the puncture site is placed, wherein the component has an opening such that the puncture site is brought into contact with the puncture tool, the container, the gauze, or the seal through the opening.

13. The blood collection apparatus according to claim 1, wherein a planned puncture point is fixed at a lowest position in the puncture site when the puncture site is fixed to the puncture site holding mechanism.

14. The blood collection apparatus according to claim 1, wherein the container is covered with a lid by arranging a cover that holds the lid of the container above the container and vertically moving the container by the driving mechanism.

15. The blood collection apparatus according to claim 14, further comprising:

a void in a part of the container holding mechanism; and a component that comes into contact with the container through the void, wherein the container rotates and revolves when the container holding mechanism is rotated by the driving mechanism.

16. The blood collection apparatus according to claim 1, wherein the container includes a linear groove, a tapered groove, or a linear or tapered protruding guide at a contact portion with the puncture site.

17. The blood collection apparatus according to claim 1, wherein the driving mechanism is operated by a mechanical power source.

* * * * *